US012415859B2

(12) United States Patent
Alfonso Martin et al.

(10) Patent No.: US 12,415,859 B2
(45) Date of Patent: Sep. 16, 2025

(54) METHODS OF PRODUCING HETERODIMERIC ANTIBODIES

(71) Applicant: GENMAB A/S, Valby (DK)

(72) Inventors: Pedro Jose Alfonso Martin, Wayne, PA (US); Michael Capaldi, Chalfont, PA (US); Jeffrey Cohen, Kennett Square, PA (US); Andrew Detzel, Media, PA (US); Joseph Sakyiama, Lower Gwynedd, PA (US)

(73) Assignee: GENMAB A/S, Valby (DK)

( * ) Notice: Subject to any disclaimer, the term of this patent is extended or adjusted under 35 U.S.C. 154(b) by 437 days.

(21) Appl. No.: 16/717,189

(22) Filed: Dec. 17, 2019

(65) Prior Publication Data

US 2020/0190200 A1 Jun. 18, 2020

Related U.S. Application Data

(60) Provisional application No. 62/781,180, filed on Dec. 18, 2018.

(51) Int. Cl.
*C07K 16/28* (2006.01)

(52) U.S. Cl.
CPC ...... *C07K 16/2863* (2013.01); *C07K 16/2809* (2013.01); *C07K 16/2866* (2013.01); *C07K 16/2878* (2013.01); *C07K 2317/10* (2013.01); *C07K 2317/31* (2013.01); *C07K 2317/526* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 2,592,668 A | 4/1952 | Dufour | |
| 5,292,668 A | 3/1994 | Paulus | |
| 5,731,168 A | 3/1998 | Carter et al. | |
| 5,807,706 A | 9/1998 | Carter et al. | |
| 6,528,286 B1 | 3/2003 | Ryll | |
| 6,737,056 B1 | 5/2004 | Presta | |
| 6,822,075 B2 | 11/2004 | Bjorck et al. | |
| 7,537,930 B2 | 5/2009 | Goldenberg et al. | |
| 7,723,485 B2 | 5/2010 | Junutula et al. | |
| 7,960,512 B2 | 6/2011 | Stavenhagen et al. | |
| 8,236,931 B2 | 8/2012 | De Wildt et al. | |
| 8,586,713 B2 | 11/2013 | Davis et al. | |
| 8,911,726 B2 | 12/2014 | Takahashi et al. | |
| 9,062,120 B2 | 6/2015 | Hunter et al. | |
| 9,150,663 B2 | 10/2015 | Abrijn et al. | |
| 9,212,230 B2 | 12/2015 | Schuurman et al. | |
| 9,540,433 B2 | 1/2017 | Verploegen et al. | |
| 9,580,508 B2 | 2/2017 | Chiu et al. | |
| 9,593,164 B2 | 3/2017 | Chiu et al. | |
| 9,595,164 B2 | 3/2017 | Robbins et al. | |
| 9,695,242 B2 | 7/2017 | Chiu et al. | |
| 9,850,310 B2 | 12/2017 | Gaudet et al. | |
| 9,896,513 B2 | 2/2018 | Krogh et al. | |
| 9,955,369 B2 | 4/2018 | Chen et al. | |
| 10,239,952 B2 | 3/2019 | Scheinberg et al. | |
| 10,344,050 B2 | 7/2019 | Gramer et al. | |
| 10,590,206 B2 | 3/2020 | Labrijn et al. | |
| 10,597,464 B2 | 3/2020 | Labrijn et al. | |
| 10,759,867 B2 | 9/2020 | Parren et al. | |
| 10,865,253 B2 | 12/2020 | Labrijn et al. | |
| 10,906,991 B2 | 2/2021 | Schuurman et al. | |
| 11,180,572 B2 | 11/2021 | De Jong et al. | |
| 11,485,796 B2 | 11/2022 | Labrijn et al. | |
| 11,492,371 B2 * | 11/2022 | Gramer | C07K 1/1133 |
| 11,866,514 B2 | 1/2024 | Labrijn et al. | |
| 12,049,512 B2 | 7/2024 | Parren et al. | |
| 12,173,076 B2 | 12/2024 | Beurskens et al. | |
| 12,247,065 B2 | 3/2025 | Hibbert et al. | |
| 2004/0038894 A1 | 2/2004 | Daeron et al. | |
| 2005/0037000 A1 | 2/2005 | Stavenhagen et al. | |
| 2005/0208519 A1 | 9/2005 | Liew et al. | |
| 2006/0074225 A1 | 4/2006 | Chamberlain et al. | |
| 2006/0134105 A1 | 6/2006 | Lazar et al. | |
| 2006/0194280 A1 | 8/2006 | Dillon et al. | |
| 2007/0287170 A1 | 12/2007 | Davis et al. | |
| 2008/0051469 A1 | 2/2008 | Brahmbhatt et al. | |
| 2009/0042253 A1 | 2/2009 | Hiller | |
| 2009/0182127 A1 | 7/2009 | Kjaergaard et al. | |
| 2009/0202546 A1 | 8/2009 | Harris et al. | |
| 2010/0015133 A1 | 1/2010 | Igawa et al. | |
| 2010/0028637 A1 | 2/2010 | Tavsanli et al. | |
| 2010/0105874 A1 | 4/2010 | Schuurman et al. | |

(Continued)

FOREIGN PATENT DOCUMENTS

AU 2017/261467 A1 11/2017
DE 19859115 A1 3/2000

(Continued)

OTHER PUBLICATIONS

Samuelson et al, Disulfide bonded protein production in *E. coli*, Genetic Engineering & Biotechnology News, Feb. 2012. (Year: 2012).*
Parren, Paul, "UniBody, a novel nonactivating antibody format," Beyond Antibodies, slideshow, 35 pages (2009).
Rispens, Theo et al., "Human IgG4 Binds to IgG4 and Conformationally Altered IgG1 via Fc-Fc Interactions," The Journal of Immunology, vol. 182:4275-4281 (2009).
Rispens, Theo, "IgG4: an odd antibody, Fc interactions and the relation to half-molecule exchange," Sanquin, slideshow, 42 pages (2009).
Robinson et al., "Targeting ErbB2 and ErbB3 with a bispecific single-chain Fv enhances targeting selectivity and induces a therapeutic effect in vitro," Br. J. Cancer, vol. 99:1415-1425 (2008).

(Continued)

*Primary Examiner* — Gary B Nickol
*Assistant Examiner* — Cheom-Gil Cheong
(74) *Attorney, Agent, or Firm* — Nelson Mullins Riley & Scarborough LLP; Jane E. Remillard, Esq.; Christopher L. Frank

(57) ABSTRACT

The invention relates to methods of producing heterodimeric antibodies.

36 Claims, 8 Drawing Sheets

Specification includes a Sequence Listing.

(56) References Cited

U.S. PATENT DOCUMENTS

| | | |
|---|---|---|
| 2010/0331527 A1 | 12/2010 | Davis et al. |
| 2011/0123532 A1 | 5/2011 | Gurney et al. |
| 2012/0149876 A1 | 6/2012 | Von Kreudenstein et al. |
| 2013/0039913 A1 | 2/2013 | Labrijn et al. |
| 2013/0177555 A1 | 7/2013 | Wilkinson et al. |
| 2013/0195849 A1 | 8/2013 | Spreter Von Kreudenstein et al. |
| 2014/0141000 A1 | 5/2014 | Chiu et al. |
| 2014/0170148 A1 | 6/2014 | De Goeij et al. |
| 2014/0170149 A1 | 6/2014 | Neijssen et al. |
| 2014/0242075 A1 | 8/2014 | Parren et al. |
| 2014/0273092 A1 | 9/2014 | Flikweert et al. |
| 2014/0303356 A1 | 10/2014 | Gramer et al. |
| 2015/0175692 A1* | 6/2015 | Di Padova ............ A61P 17/06 530/387.3 |
| 2015/0175707 A1 | 6/2015 | De Jong et al. |
| 2015/0337049 A1 | 11/2015 | Labrijn et al. |
| 2015/0353636 A1 | 12/2015 | Parren et al. |
| 2016/0046727 A1 | 2/2016 | Labrijn et al. |
| 2016/0159930 A1 | 6/2016 | Schuurman et al. |
| 2017/0233497 A1 | 8/2017 | Labrijn et al. |
| 2017/0327597 A1 | 11/2017 | Labrijn et al. |
| 2017/0369590 A1 | 12/2017 | De Goeij et al. |
| 2018/0118849 A1 | 5/2018 | Klein et al. |
| 2018/0201693 A1 | 7/2018 | Hibbert et al. |
| 2019/0352423 A1 | 11/2019 | De Goeij et al. |
| 2020/0048304 A1 | 2/2020 | Gramer et al. |
| 2020/0181277 A1 | 6/2020 | Beurskens et al. |
| 2020/0262932 A1 | 8/2020 | Labrijn et al. |
| 2020/0332022 A1 | 10/2020 | Labrijn et al. |
| 2021/0107988 A1 | 4/2021 | Oostindie et al. |
| 2021/0163619 A1 | 6/2021 | Parren et al. |
| 2021/0230301 A1 | 7/2021 | De Jong et al. |
| 2021/0269509 A1 | 9/2021 | Hibbert et al. |
| 2023/0227495 A1 | 7/2023 | Gramer et al. |
| 2023/0322947 A1 | 10/2023 | Labrijn et al. |
| 2024/0209117 A1 | 6/2024 | Labrijn et al. |
| 2025/0043018 A1 | 2/2025 | Parren et al. |

FOREIGN PATENT DOCUMENTS

| | | | |
|---|---|---|---|
| EP | 1693386 | A1 | 8/2006 |
| EP | 1870459 | A1 | 12/2007 |
| JP | 2015143238 | A | 8/2015 |
| WO | 1988/01649 | A1 | 3/1988 |
| WO | 1992/01047 | A1 | 1/1992 |
| WO | 1994/13804 | A1 | 6/1994 |
| WO | 96/27011 | A1 | 9/1996 |
| WO | 98/04592 | A1 | 2/1998 |
| WO | 1998/44001 | A1 | 10/1998 |
| WO | 98/50431 | A2 | 11/1998 |
| WO | 9955369 | A1 | 11/1999 |
| WO | 02/100348 | A2 | 12/2002 |
| WO | 2004/035607 | A2 | 4/2004 |
| WO | 2005/000899 | A2 | 1/2005 |
| WO | 2005/062916 | A2 | 7/2005 |
| WO | 2006/047340 | A2 | 5/2006 |
| WO | 2006/106905 | A1 | 10/2006 |
| WO | 2007/059782 | A1 | 5/2007 |
| WO | 2007/103112 | A2 | 9/2007 |
| WO | 2007/110205 | A2 | 10/2007 |
| WO | 2007147901 | A1 | 12/2007 |
| WO | 2008/052933 | A2 | 5/2008 |
| WO | 2008/119353 | A1 | 10/2008 |
| WO | 2008/145140 | A2 | 12/2008 |
| WO | 2008/145142 | A1 | 12/2008 |
| WO | 2009009407 | A1 | 1/2009 |
| WO | 2009/080251 | A1 | 7/2009 |
| WO | 2009/085462 | A1 | 7/2009 |
| WO | 2009/089004 | A1 | 7/2009 |
| WO | 2010/001251 | A2 | 1/2010 |
| WO | 2010/063785 | A2 | 6/2010 |
| WO | 2010/129304 | A2 | 11/2010 |
| WO | 2010/151792 | A1 | 12/2010 |
| WO | 2011/131746 | A2 | 10/2011 |
| WO | 2011/133886 | A2 | 10/2011 |
| WO | 2011/143545 | A1 | 11/2011 |
| WO | 2012/058768 | A1 | 5/2012 |
| WO | 2012/116453 | A1 | 9/2012 |
| WO | 2012/143524 | A2 | 10/2012 |
| WO | 2013/060867 | A2 | 5/2013 |
| WO | 2013088259 | A2 | 6/2013 |
| WO | 2013096291 | A2 | 6/2013 |
| WO | 2013/136186 | A2 | 9/2013 |
| WO | 2013157954 | A1 | 10/2013 |
| WO | 2016/097300 | A1 | 6/2016 |
| WO | 2017/005649 | A1 | 1/2017 |

OTHER PUBLICATIONS

Rudikoff, S. et al., "Single amino acid substitution altering antigen-binding specificity," Proc Natl Acad Sci USA, vol. 79:1979-1983 (1982).

Santora, L.C. et al., "Characterization of recombinant human monoclonal tissue necrosis factor-alpha antibody using cation-exchange HPLC and capillary isoelectric focusing," Analytical Biochemistry, vol. 275: 98-108 (1999).

Schuurman, J. et al., "Normal human immunoglobulin G4 is bispecific: it has two different antigen-combining sites," Immunology, vol. 97:693-698 (1999).

Schuurman, Janine et al., "Anti-Inflammatory Activity of Human IgG4 Antibodies by Dynamic Fab Arm Exchange," World BioPharm Forum, Poster, 1 page (2009).

Schuurman, Janine et al., "The inter-heavy chain disulfide bonds of IgG4 are in equilibrium with intra-chain disulfide ponds," Molecular Immunology, vol. 38:1-8 (2001).

Schuurman, Janine, "IgG4 Fab-arm exchange," World BioPharm Forum, slideshow, 26 pages (2009).

Schuurman, Janine, "Post-Transcriptional Modifications," Genmab, slideshow, 43 pages (2008).

Schuurman, Janine, "The impact of Fab-arm exchange on the development of antibody therapeutics, " Antibody Discovery & Development Forum, slideshow, 30 pages (2011).

Schuurman, Janine, "The impact of Fab-arm exchange on the development of antibody therapeutics," Antibody Engineering and Design, slideshow, 29 pages (2011).

Schuurman, Janine, "The impact of Fab-arm exchange on the development of antibody therapeutics," Genmab, slideshow, 30 pages (2010).

Scinicariello, F. et al., "Rhesus macaque antibody molecules: sequences and heterogeneity of alpha and gamma constant regions," Immunol., vol. 111:66-74 (2004).

Shatz, W et al., "An efficient route to bispecific antibody production using single-reactor mammalian co-culture," mAbs, vol. 8(8):1487-1497 (2016).

Skolnick, J. et al., "From genes to protein structure and function: novel applications of computational approaches in the genomic era," Trends Biotechnol., vol. 18(1):34-39) (2000).

Stubenrauch, Kay et al., "Impact of Molecular Processing in the Hinge Region of Therapeutic IgG4 Antibodies on Disposition Profiles in Cynomolgus Monkeys," Drug Metabolism and Disposition, vol. 38(1):84-91 (2010).

Tao, M. et al. "Structural Features of Human Immunoglobulin G that Determine Isotype-specific Differences in Complement Activation," Journal of Experimental Medicine, vol. 178:661-667 (1993).

Vajdos, F. et al., "Comprehensive functional maps of the antigen-binding site of an anti-ErbB2 antibody obtained with shotgun scanning mutagenesis," J Mol Biol., vol. 320(2):415-428 (2002).

Van Berkel, Patrick H.C., "Development of a production process for DuoBody: a novel human bispecific platform," Informa/IBC Life Sciences' Bioproduction Conference, Poster, 1 page (2011).

Van De Winkel, Jan et al., "Better Antibodies by Design, 2011 R&D Day," slideshow, 109 pages (2011).

Van Der Neut Kolfschoten, Marijn et al., "Anti-Inflammatory Activity of Human IgG4 Antibodies by Dynamic Fab Arm Exchange," Science, vol. 317:1554-1557 (2007).

Van Der Zee, J.S. et al., "Inhibition of complement activation by IgG4 antibodies," Clin. exp. Immunol., vol. 64:415-422 (1986).

(56) References Cited

OTHER PUBLICATIONS

Van Der Zee, Jaring S. et al., "Serologic Aspects of IgG4 Antibodies. II. IgG4 Antibodies Form Small, Nonprecipitating Immune Complexes Due to Functional Monovalency," The Journal of Immunology, vol. 137(11):3566-3571 (1986).
Wu, H. et al., "Humanization of a murine monoclonal antibody by simultaneous optimization of framework and CDR residues," J Mol Biol., vol. 294: 151-162 (1999).
Yu, L. et al., "Interaction between bevacizumab and murine VEGF-A: a reassessment," Investigative Ophthalmology & Visual Science, vol. 49(2): 522-527 (2008).
Zuckier et al., "Chimeric human-mouse IgG antibodies with shuffled constant region exons demonstrate that multiple domains contribute to in vivo half-life," Cancer Research, 58:3905-3908 (1998).
Baert, F. et al., "Influence of immunogenicity on the long-term efficacy of infliximab in Crohn's disease," N Engl J Med., vol. 348:601-608 (2003).
Chothia, C. et al., "Canonical structures for the hypervariable regions of immunoglobulins," J Mol Biol., vol. 196: 901-917 (1987).
Gramer, M. et al., "Production of stable bispecific IgG1 by controlled Fab-arm exchange: scalability from bench to large-scale manufacturing by application of standard approaches," MAbs, vol. 5:962-973 (2013).
Honegger, A. et al., "Yet another numbering scheme for immunoglobulin variable domains: an automatic modeling and analysis tool," J Mol Biol., vol. 309:657-670 (2001).
Knappik, A. et al., "Fully synthetic human combinatorial antibody libraries (HuCAL) based on modular consensus frameworks and CDRs randomized with trinucleotides," J Mol Biol., vol. 296:57-86 (2000).
Lefranc, M-P. et al., "IMGT, the international ImMunoGeneTics database," Dev Comp Immunol., vol. 27: 55-77 (2003).
Martin, A. et al., "Structural families in loops of homologous proteins: automatic classification, modeling and application to antibodies," J Mol Biol., vol. 263: 800-815 (1996).
Stickler, M. et al., "The human G1m1 allotype associates with CD4+ T-cell responsiveness to a highly conserved IgG1 constant region peptide and confers an asparaginyl endopeptidase cleavage site," Genes and Immunity, vol. 12:213-221 (2011).
Wu, T. et al., "An analysis of the sequences of the variable regions of Bence Jones proteins and myeloma light chains and their implications for antibody complementarity," J Exp Med., vol. 132: 211-250 (1970).
Shi, L. et al., "De novo selection of high-affinity antibodies from synthetic fab libraries displayed on phage as pIX fusion proteins," J Mol Biol., vol. 397:385-396 (2010).
U.S. Appl. No. 15/742,803, filed Jan. 8, 2018, Richard G. Hibbert.
U.S. Appl. No. 15/536,143, filed Jun. 15, 2017, Aran F. Labrijn.
U.S. Appl. No. 14/353,962, filed Apr. 24, 2014, Michael Gramer.
U.S. Appl. No. 16/426,647, filed May 30, 2019, Michael Gramer.
U.S. Appl. No. 16/777,053, filed Jan. 30, 2020, Aran Frank Labrijn.
U.S. Appl. No. 15/414,122, filed Jan. 24, 2017, Aran Frank Labrijn.
U.S. Appl. No. 14/830,336, filed Aug. 19, 2015, Aran Frank Labrijn.
U.S. Appl. No. 13/642,253, filed Oct. 24, 2012, Aran Frank Labrijn.
U.S. Appl. No. 14/934,956, filed Nov. 6, 2015, Janine Schuurman.
U.S. Appl. No. 12/593,759, filed Jan. 6, 2010, Janine Schuurman.
U.S. Appl. No. 16/921,154, filed Jul. 6, 2020, Paul Parren.
U.S. Appl. No. 14/130,543, filed May 5, 2014, Paul Parren.
U.S. Appl. No. 14/413,178, filed Mar. 17, 2015, Rob N. De Jong.
U.S. Appl. No. 17/012,102, filed Sep. 4, 2020, Rob N. De Jong.
U.S. Appl. No. 16/783,720, filed Feb. 6, 2020, Aran Frank Labrijn.
U.S. Appl. No. 14/760,157, filed Jul. 9, 2015, Aran Frank Labrijn.
U.S. Appl. No. 16/482,747, filed Aug. 1, 2019, Frank Beurskens.
U.S. Appl. No. 16/963,701, filed Jul. 21, 2020, Simone Oostindie.
U.S. Appl. No. 17/253,286, filed Dec. 17, 2020, Richard Hibbert.
Aalberse, Rob C. et al., "IgG4 breaking the rules," Immunology, vol. 105:9-19 (2002).

Aalberse, Rob C. et al., "Serologic Aspects of IgG4 Antibodies. I. Prolonged Immunization Results in an IgG4-Restricted Response," The Journal of Immunology, vol. 130(2):722-726 (1983).
Aalberse, Rob C. et al., "The Apparent Monovalency of Human IgG4 Is Due to Bispecificity," Int. Arch. Allergy Immunol., vol. 118:187-189 (1999).
Aalberse, Rob C., "Physiological Fab arm exchange of IgG4 generates an anti-inflammatory antibody," Genmab, European Antibody Congress, 36 pages (2008).
Angal, S. et al., "A Single Amino Acid Substitution Abolishes the Hetergeneity of Chimeric Mouse/Human (IgG4) Antibody," Molecular Immunology, vol. 30(1):105-108 (1993).
Bloom, James W. et al., "Intrachain disulfide bond in the core hinge region of human IgG4," Protein Science, vol. 6:407-415 (1997).
Bork, P., "Powers and pitfalls in sequence analysis: the 70% hurdle," Genonne Research, vol. 10:398-400 (2000).
Brown, M. et al., "Tolerance of single, but not multiple, amino acid replacements in antibody VH CDR 2: a means of minimizing B cell wastage from somatic hypermutation?," J Immunol., vol. 156(9):3285-3291 (1996).
Brusco et al., "Molecular characterization of immunoglobulin G4 gene isoallotypes," Eur J Immnogene, 25:349-355 (1998).
Burgess, W. et al., "Possible dissociation of the heparin-binding and mitogenic activities of heparin-binding (acidic fibroblast) growth factor-1 from its receptor-binding activities by site-directed mutagenesis of a single lysine residue," J. Cell Biol., vol. 111:2129-2138(1990).
Carlring, Jennifer et al., "A Novel Redox Method for Rapid Production of Functional Bi-Specific Antibodies For Use in Early Pilot Studies," PLoS One, vol. 6(7):e22533, pp. 1-6 (2011).
Chames, P. et al., "Bispecific Antibodies for Cancer Therapy" Curr. Opin Drug Discvo. Devel, vol. 12(2):276-283 (2009).
Ciccimarra, F. et al., "Localization of the IgG effector site for monocyte receptors," PNAS, 72:2081-2083(1975).
Dall'Acqua, William et al., "Contribution of Domain Interface Residues to the Stability of Antibody CH3 Domain Homodimers," Biochemistry, vol. 37:9266-9273 (1998).
Deng, Liang et al., "Detection and quantification of the human IgG4 half-molecule, HL, from unpurified cell-culture supernatants," Biotechnol. Appl. Biochem., vol. 40:261-269 (2004).
Dick, L. et al., "C-terminal lysine variants in fully human monoclonal antibodies: investigation of test methods and possible causes," Biotechnology and Bioengineering, vol. 100(6): 1132-1143 (2008).
Genmab, "Better Antibodies by Design," www.genmab.com, 2 pages (2011).
Genmab, "Building for a Commercial Future: Research, Development and Business Update," slideshow, 65 pages (2006).
Genmab, "DuoBody platform, Genmab's proprietary bispecific antibody platform," slideshow, 15 pages, (2011).
Genmab, "DuoBody, The next generation of therapeutic antibodies," www.genmab.com, 2 pages (2011).
Genmab, "DuoBody: Innovative Bispecific Antibody Platform," Poster for R&D Day, 1 page (2011).
Genmab, "Genmab, Beter Antibodies by Design," slideshow, 2 pages (2011).
Genmab, "The physiological generation of bispecific IgG4 antibodies," Sanquin Spring Symposium, slideshow, 54 pages (2007).
Genmab, "Therapeutic IgG4 antibodies engage in Fab-arm exchange with patients' IgG4 in vivo," Antibodies as Drugs, Poster #214, 14 pages (2009).
Gunasekaran, K. et al., "Enhancing Antibody Fc Heterodimer Formation through Electrostatic Steering Effects: Applications to Bispecific Molecules and Monovalent IgG," Journal of Biological Chemistry, vol. 285 (25):19637-19646 (2010).
Hay, M. et al., "Clinical development success rates for investigational drugs," Nature Biotechnology, vol. 32(1): 40-51 (2014).
International Preliminary Report on Patentability, PCT/EP2012/071294, dated Apr. 29, 2014, pp. 1-13.
International Preliminary Report on Patentability, PCT/IB2019/060969, dated Jun. 16, 2021, 9 pages.
International Preliminary Report on Patentabilty, PCT/EP2015/080509, dated Jun. 20, 2017, 9 pages.
International Search Report and Written Opinion, PCT/EP2012/071294, dated Apr. 26, 2013, pp. 1-20.

(56) References Cited

OTHER PUBLICATIONS

International Search Report and Written Opinion, PCT/EP2015/080509, dated Mar. 30, 2016, 13 pages.
International Search Report and Written Opinion, PCT/IB2019/060969, dated Jul. 14, 2020, 12 pages.
Junttila, T. et al., "Antitumor Efficacy of a Bispecic Antibody That Targets HER2 and Activates T Cells," American Association for Cancer Research, vol. 74(19): 5561-5571 (2014).
Klein, C. et al., "Progress in overcoming the chain association issue in bispecific heterodimeric IgG antibodies," mAbs, vol. 4(6):653-663 (2012).
Labrijn et al., "Controlled fab-arm exchange for the generation of stable bispecific IgG1," Nature Protocols, vol. 9(10): 2450-2463 (2014).
Labrijn et al., "Efficient generation of stable bispecific IgG1 by controlled Fab-arm exchange," Proc Natl Acad Sci., vol. 110(13):5145-5150 (2013).
Labrijn, Aran F. et al., "Species-Specific Determinants in the IgG CH3 Domain Enable Fab-Arm Exchange by Affecting the Noncovalent CH3—CH3 Interaction Strength," The Journal of Immunology, vol. 187, 9 pages (2011).
Labrijn, Aran F. et al., "Species-specific determinants in the immunoglobulin CH3 domain enable Fab-arm exchange by affecting the non-covalent CH3—CH3 interaction strength," Keystone Symposium, Antibodies as Drugs Poster Presentation, 1 page (2011).
Labrijn, Aran F. et al., "Therapeutic IgG4 antibodies engage in Fab-arm exchange with endogenous human IgG4 in vivo," Nature Biotechnology, vol. 27(8):767-771 (2009).
Lewis, Kenneth B. et al., "Comparison of the ability of wild type and stabilized human IgG4 to undergo Fab arm exchange with endogenous IgG4 in vitro and in vivo," Molecular Immunology, vol. 46:3488-3494 (2009).
Lindhofer, H. et al., "Preferential species-restricted heavy/light chain pairing in rat/mouse quadromas. Implications for a single-step purification of bispecific antibodies," J Immunol., vol. 155(1):219-225 (1995).
Lund, J. et al., "Multiple interactions of IgG with its core oligosaccharide can modulate recognition by complement and human Fc gamma receptor I and influence the synthesis of its oligosaccharide chains," The Journal of Immunology, vol. 157:4963-4969 (1996).
Marvin, Jonathan S. et al., "Recombinant approaches to IgG-like bispecific antibodies," Acta Pharmacologica Sinica, vol. 26(6):649-658 (2005).
Merchant, A. Margaret et al., "An efficient route to human bispecific IgG," Nature Biotechnology, vol. 16:677-681 (1998).
Milstein C. et al., "Hybrid hybridomas and their use in immunohistochemistry," Nature, vol. 305(5934):537-540 (1983).
Miosge, L. et al., "Comparison of predicted and actual consequences of missense mutations," Proc Natl Acad Sci U S A., vol. 112(37):E5189-E5198 (2015).
Mori, Katsuhiro et al., "Non-fucosylated therapeutic antibodies: the next generation of therapeutic antibodies," Cytotechnology, vol. 55:109-114 (2007).
Nilson, B.H.K et al., "Purification of antibodies using protein L-binding framework structures in the light chain variable domain," Journal of Immunological Methods, vol. 164(1): 33-40 (1993).
Doijevaar-De Heer, Pleuni G. et al., "Fc binding activity of IgG4 is a confounding factor in the measurement of IgG4 bispecificity," Sanquin Spring Symposium, 1 page (2007).
U.S. Appl. No. 17/950,350, filed Sep. 22, 2022, Aran Frank Labrijn.
Kuo, T.T. et.al . "Neonatal Fc receptor and IgG-based therapeutics," MABS, vol. 3(5): 422-430 (2011).

* cited by examiner

METHODS OF PRODUCING HETERODIMERIC ANTIBODIES

CROSS-REFERENCE TO RELATED APPLICATIONS

This application claims the benefit of U.S. Provisional Application Ser. No. 62/781,180, filed 18 Dec. 2018, the entire contents of which are incorporated herein by reference.

FIELD OF THE INVENTION

The invention relates to methods of producing heterodimeric antibodies.

SEQUENCE LISTING

This application contains a Sequence Listing submitted via EFS-Web, the entire content of which is incorporated herein by reference. The ASCII text file, created on 10 December 2019, is named JBI6029USNP1_ST25.txt and is 21 kilobytes in size.

BACKGROUND OF THE INVENTION

Monoclonal antibodies have demonstrated success as therapeutic molecules, especially in the treatment of cancer. Bispecific antibodies are expected to increase the potency and efficacy of monoclonal antibody therapies as they may be used to direct a drug or toxic compound to target cells, to redirect effector mechanisms to disease-associated sites or to increase specificity for tumor cells, for example by binding to one or more target molecules that are expressed on tumor cells. Further, by combining the specificity of two monoclonal antibodies in one, bispecific antibodies could potentially engage a greater array of mechanisms of action.

Different formats of bispecific antibodies and methods of producing them have been described, however a challenge exists to produce the bispecific antibodies in large scale by optimizing manufacturing processes.

BRIEF SUMMARY OF THE INVENTION

The invention provides a method of producing a heterodimeric antibody, comprising
providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that a heterodimeric interaction between the first CH3 region and the second CH3 region is stronger than a homodimeric interaction between the first CH3 region or a homodimeric interaction between the second CH3 region;
combining the first homodimeric antibody and the second homodimeric antibody into a mixture; and
incubating the mixture in the presence of a reducing agent and ambient dissolved oxygen ($DO_2$) to produce the heterodimeric antibody, wherein the method lacks one or more steps of measuring a percentage (%) $DO_2$ in the mixture, controlling the % $DO_2$ in the mixture, or adding oxygen into the mixture during producing the heterodimeric antibody.

The invention also provides a method of producing a heterodimeric antibody, comprising
providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that the heterodimeric interaction between the first CH3 region and the second CH3 region is stronger than a homodimeric interaction between the first CH3 region or a homodimeric interaction between the second CH3 region;
combining the first homodimeric antibody and the second homodimeric antibody into a mixture;
incubating the mixture in the presence of a reducing agent; and
removing the reducing agent to produce the heterodimeric antibody, wherein the percentage (%) of dissolved oxygen ($DO_2$) is controlled to be about 30% or lower during step of incubating the mixture in the presence of the reducing agent, during step of removing the reducing agent to produce the heterodimeric antibody, or during steps of incubating the mixture in the presence of the reducing agent and removing the reducing agent to produce the heterodimeric antibody.

DETAILED DESCRIPTION OF THE INVENTION

Definitions

Figure 1:
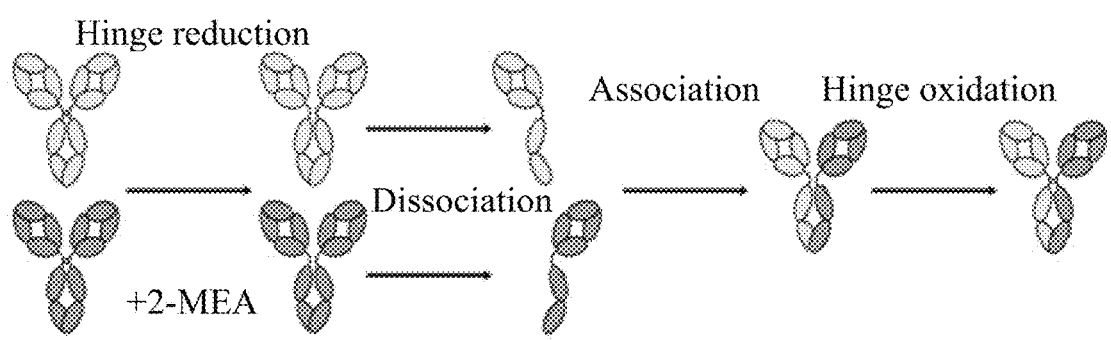
FIG. 1 shows a summary of Fab-arm exchange.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Antibodies" refer to immunoglobulin molecules having two heavy chains (HC) and two light chains (LC) interconnected by disulfide bonds. Each heavy chain is comprised of a heavy chain variable region (VH) and a heavy chain constant region, the heavy chain constant region divided into regions CH1, hinge, CH2 and CH3. Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Antibodies include monoclonal antibodies including murine, human, humanized and chimeric antibodies, bispecific or multispecific antibodies.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Biol* 196:901-17), IMGT (Lefranc et al. (2003) *Dev Comp Immunol* 27:55-77) and AbM (Martin and Thornton (1996) *J Bmol Biol* 263:800-15). The correspondence between the various delineations and variable region numbering are described (see e.g. Lefranc et al. (2003) *Dev Comp Immunol* 27:55-77; Honegger and Pluckthun, *J Mol Biol* (2001) 309:657-70; International ImMunoGeneTics (IMGT) database; Web resources, www.imgt.org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Immunoglobulins may be assigned to five major classes, IgA, IgD, IgE, IgG and IgM, depending on the heavy chain constant region amino acid sequence. IgA and IgG are further sub-classified as isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Fab-arm" refers to one heavy chain-light chain pair of an antibody.

"Homodimerization" refers to an interaction of two heavy chains having identical CH3 amino acid sequences.

"Homodimer" refers to an antibody having two heavy chains which have identical CH3 region amino acid sequences.

"Heterodimerization" refers to an interaction of two heavy chains having non-identical CH3 amino acid sequences.

"Heterodimer" refers to an antibody having two heavy chains which differ in their amino acid sequence in the CH3 region by one or more amino acids.

"Fc region" or "Fc domain" refers to an antibody region comprising at least a portion of a hinge region, a CH2 region and a CH3 region. The Fc region may be generated by digestion of an antibody with papain, or pepsing where the Fc region is the fragment obtained thereby, which includes one or both CH2-CH3 regions of an immunoglobulin and a portion of the hinge region. The constant domain of an antibody heavy chain defines the antibody isotype, e.g. IgG1, IgG2, IgG3, IgG4, IgA1, IgA2, IgE. The Fc-region mediates the effector functions of antibodies with cell surface Fc receptors and proteins of the complement system.

"CH1 region" or "CH1 domain" refers to the CH1 region of an immunoglobulin. The CH1 region of a human IgG1 antibody corresponds to amino acid residues 118-215. However, the CH1 region may also be any of the other antibody isotypes as described herein.

"CH2 region" or "CH2 domain" refers to the CH2 region of an immunoglobulin. The CH2 region of a human IgG1 antibody corresponds to amino acid residues 231-340. However, the CH2 region may also be any of the other antibody isotypes as described herein.

"CH3 region" or "CH3 domain" refers to the CH3 region of an immunoglobulin. The CH3 region of human IgG1 antibody corresponds to amino acid residues 341-446. However, the CH3 region may also be any of the other antibody isotypes as described herein.

"Hinge" or "hinge region" refers to the hinge region of an immunoglobulin. The hinge region of human IgG1 antibody generally corresponds to amino acids 216-230 according of the EU numbering system. "Hinge" may also be considered to include additional residues termed the upper and lower hinge regions, such as from amino acid residues 216 to 239.

"Mixture" refers to an aqueous solution of two or more antibodies.

"Reducing agent" regers to an agent that is capable of reducing the inter-chain disulfide bonds in the hinge region of an antibody.

"GMP-compliant conditions" refers to manufacturing under good manufacturing practice (CGMP) regulations enforced by the FDA. CGMPs provide for systems that assure proper design, monitoring, and control of manufacturing processes and facilities. Adherence to the CGMP regulations assures the identity, strength, quality, and purity of drug products by requiring that manufacturers of medications adequately control manufacturing operations. This includes establishing strong quality management systems, obtaining appropriate quality raw materials, establishing robust operating procedures, detecting and investigating product quality deviations, and maintaining reliable testing laboratories. This formal system of controls at a pharmaceutical company, if adequately put into practice, helps to prevent instances of contamination, mix-ups, deviations, failures, and errors. This assures that drug products meet their quality standards.

"Drug substance" or "DS" refers to Any substance or mixture of substances intended to be used in the manufacture of a drug (medicinal) product and that, when used in the production of a drug, becomes an active ingredient of the drug product. Such substances are intended to furnish pharmacological activity or other direct effect in the diagnosis, cure, mitigation, treatment, or prevention of disease or to affect the structure or function of the body.

"Drug product" or "DP" refers to a finished dosage form, for example, a tablet, capsule or solution that contains an active pharmaceutical ingredient (e.g. drug substance), generally, but not necessarily, in association with inactive ingredients.

"Reference product" refers to an approved biological product against which a biosimilar product is compared. A reference product is approved based on, among other things, a full complement of safety and effectiveness data and is approved in at least one of the U.S., Europe, or Japan.

"Bio similar" (of an approved reference product/biological drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar must have been previously approved for the reference product. The route of administration, the dosage form, and/or the strength of the biosimilar must be the same as those of the reference product and the biosimilar must be manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance. The reference product may be approved in at least one of the U.S., Europe, or Japan.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) *J Mol Biol* 296:57-86, or synthetic HCDR3 incorporated into human immunoglobulin gene libraries displayed on phage, for example as described in Shi et al., (2010) *J Mol Biol* 397:385-96, and in WO2009/085462. Antibodies in which at least one CDR is derived from a non-human species are not included in the definition of "human antibody".

"Recombinant" refers to DNA, antibodies and other proteins that are prepared, expressed, created or isolated by recombinant means when segments from different sources are joined to produce recombinant DNA, antibodies or proteins. "Recombinant antibody" includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Bispecific" refers to an antibody that specifically binds two distinct antigens or two distinct epitopes within the same antigen. The bispecific antibody may have cross-reactivity to other related antigens or can bind an epitope that is shared between two or more distinct antigens.

"Multispecific" refers to an antibody that specifically binds at least two distinct antigens or at least two distinct epitopes within the same antigen. Multispecific antibody may bind for example two, three, four or five distinct antigens or distinct epitopes within the same antigen.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Variant" refers to a polypeptide or a polynucleotide that differs from a reference polypeptide or a reference polynucleotide by one or more modifications for example, substitutions, insertions or deletions.

"Mutation" refers to an engineered or naturally occurring alteration in a polypeptide or polynucleotide sequence when compared to a reference sequence. The alteration may be a substitution, insertion or deletion of one or more amino acids or polynucleotides.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, MD. (1991), unless otherwise explicitly stated. Antibody constant chain numbering can be found for example at ImMunoGeneTics website, at IMGT Web resources at IMGT Scientific charts.

The mutations in the CH3 region described herein are expressed as modified position(s) in the first CH3 domain of the first heavy chain/modified position(s) in the second CH3 domain of the second heavy chain. For example, F405L/K409R refers to a F405L mutation in the first CH3 region and K09R mutation in the second CH3 region. L351Y_F405A_Y407V/T394W refers to L351Y, F40FA and Y407V mutations in the first CH3 region and T394W mutation in the second CH3 region. D399FHKRQ/K409AGRH refers to mutation in which D399 may be replaced by F, H, K R or Q, and K409 may be replaced by A, G, R or H.

Conventional one and three-letter amino acid codes are used herein as shown in Table 1.

TABLE 1

| Amino acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Methods of the Invention

The invention provides methods of producing heterodimeric antibodies using Fab-arm exchange. The invention is based on, at least in part, on the identification that, contrary to what has been disclosed in literature (see, e.g., US2014/0303356), oxygen is not required for reformation of the disulfide bonds after their reduction to form stable heterodimeric antibodies during Fab-arm exchange, hence providing alternative approaches for process control during large scale production of heterodimeric antibodies (e.g., bispecific antibodies).

The invention provides a method of producing a heterodimeric antibody, comprising providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that a heterodimeric interaction between the first CH3 region and the second CH3 region is stronger than a homodimeric interaction between the first CH3 region or a homodimeric interaction between the second CH3 region;

combining the first homodimeric antibody and the second homodimeric antibody into a mixture; and incubating the mixture in the presence of a reducing agent and ambient dissolved oxygen ($DO_2$) to produce the heterodimeric antibody, wherein the method lacks one or more steps of measuring a percentage (%) $DO_2$ in the mixture, controlling the % $DO_2$ in the mixture, or adding oxygen into the mixture during producing the heterodimeric antibody.

In some embodiments, the % $DO_2$ in the mixture is between about 10% and about 90% during producing the heterodimeric antibody.

In some embodiments, % $DO_2$ in the mixture is about 30% or more in the mixture piror to addition of the denaturing agent.

The invention also provides a method of producing a heterodimeric antibody, comprising providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that the heterodimeric interaction between the first CH3 region and the second CH3 region is stronger than a homodimeric interaction between the first CH3 region or a homodimeric interaction between the second CH3 region;

combining the first homodimeric antibody and the second homodimeric antibody into a mixture;

incubating the mixture in the presence of a reducing agent; and removing the reducing agent to produce the heterodimeric antibody, wherein the percentage (%) of dissolved oxygen ($DO_2$) is controlled to be about 30% or lower in step c), step d) or both in step c) and step d).

In some embodiments, the % $DO_2$ the mixture is about 25% or less, 20% or less, about 15% or less, about 10% or less, about 9% or less, about 8% or less, about 7% or less, about 6% or less, about 5% or less, about 4% or less, about 3% or less, about 2% or less or about 1% or less.

In some embodiments, % $DO_2$ is controlled by displacing oxygen from the mixture by overlaying the mixture with an inert gas such as nitrogen. The concentration of dissolved oxygen may be monitored by known methods, such as utilizing a dissolved oxygen probe.

"Stronger" in terms of the heterodimeric interaction of the first CH3 region and the second CH3 region region may be more than two times stronger, for example more than three times stronger, more than four times stronger or more than five times stronger than the strongest of the homodimeric interaction between the first CH3 region or a homodimeric interaction between the second CH3 region. The strength of the interaction of the CH3 domains may be measured using mass spectrometrly. In an exemplary assay, constructs comprising the first CH3 region and the second CH3 region or alternatively both including the CH2 region are made using standard molecular biology techniques. Samples are prepared that contain the first CH3 domain, the second CH3 domain or the first CH3 domain and the second CH3 domain and buffer-exchanged to 100 mM ammonium acetate pH 7, using 10 kDa MWCO spin-filter columns. Aliquots (1 µL) of serial diluted samples (20 µM-25 nM; monomer equivalent) are loaded into gold-plated borosilicate capillaries for analysis on a LCT mass spectrometer (Waters). The monomer signal, $M_s$, is defined as the area of the monomer peaks as a fraction of the area of all peaks in the spectrum ($M_s/(M_s+D_s)$ where $D_s$=the dimer signal). The concentration of monomer at equilibrium, $[M]_{eq}$, is defined as $M_s \cdot [M]_0$ where $[M]_0$ is the overall protein concentration in terms of monomer. The dimer concentration at equilibrium, $[D]_{eq}$, is defined as $([M]_0-[M]_{eq})/2$. The $K_D$, for the homodimerci CH3 interactiosn and the heterodimeric CH3 interactions is then extracted from the gradient of a plot of $[D]_{eq}$ versus $[M]_{eq}^2$.

In some embodiments, the first homodimeric antibody and the second homodimeric antibody are combined into the mixture at a molar ratio of about 1:1.

In some embodiments, the first homodimeric antibody and the second homodimeric antibody are combined into the mixture at the molar ratio of about 1.05:1.

In some embodiments, the first homodimeric antibody and the second homodimeric antibody are combined into the mixture at the molar ratio of between about 1:1.03 to about 1:2. In some embodiments, the first homodimeric antibody and the second homodimeric antibody are combined into the mixture at the molar ratio of between about 1:1.05 to 1:1.5. In some embodiments, the first homodimeric antibody and the second homodimeric antibody are combined into the mixture at the molar ratio of between about 1:1.1 to 1:1.5. In some embodiments, the first homodimeric antibody and the second homodimeric antibody are combined into the mixture at the molar ratio of between about 1:1.1 to 1:1.4. In some embodiments, the first homodimeric antibody and the second homodimeric antibody are combined into the mixture at the molar ratio of between about 1:1.15 to 1:1.35. In some embodiments, the first homodimeric antibody and the second homodimeric antibody are combined into the mixture at the molar ratio of between about 1:1.2 to 1:1.3.

In some embodiments, total concentration of immunoglobulin in the mixture is between about 1 g/L and 70 g/L. In some embodiments, total concentration of immunoglobulin in the mixture is between about 8 g/L and about 50 g/L. In some embodiments, total concentration of immunoglobulin in the mixture is between about 8 g/L and about 13 g/L. In some embodiments, total concentration of immunoglobulin in the mixture is about 9.0 g/L. In some embodiments, total concentration of immunoglobulin in the mixture is about 9.5 g/L. In some embodiments, total concentration of immunoglobulin in the mixture is about 10 g/L. In some embodiments, total concentration of immunoglobulin in the mixture is about 10.5 g/L. In some embodiments, total concentration of immunoglobulin in the mixture is about 11.0 g/L. In some embodiments, total concentration of immunoglobulin in the mixture is about 11.5 g/L. In some embodiments, total concentration of immunoglobulin in the mixture is about 12.0 g/L. In some embodiments, total concentration of immunoglobulin in the mixture is about 12.5 g/L. In some embodiments, total concentration of immunoglobulin in the mixture is about 13.0 g/L. In some embodiments, total concentration of immunoglobulin in the mixture is about 13.5 g/L. In some embodiments, total concentration of immunoglobulin in the mixture is about 14.0 g/L. In some embodiments, total concentration of immunoglobulin in the mixture is about 14.5 g/L. In some embodiments, total concentration of immunoglobulin in the mixture is about 15.0 g/L. In some embodiments, total concentration of immunoglobulin in the mixture is about 20.0 g/L. In some embodiments, total concentration of immunoglobulin in the mixture is about 25.0 g/L. In some embodiments, total concentration of immunoglobulin in the mixture is about 30.0 g/L. In some embodiments, total concentration of immunoglobulin in the mixture is about 35.0 g/L. In some embodiments, total concentration of immunoglobulin in the mixture is about 40.0 g/L. In some embodiments, total concentration of immunoglobulin in the mixture is about 45.0 g/L. In some embodiments, total concentration of immunoglobulin in the mixture is about 50.0 g/L. In some embodiments, total concentration of immunoglobulin in the mixture is about 55.0 g/L. In some embodiments, total concentration of immunoglobulin in the mixture is about 60.0 g/L. In some embodiments, total concentration of immunoglobulin in the mixture is about 65.0 g/L. In some embodiments, total concentration of immunoglobulin in the mixture is about 70.0 g/L.

In some embodiments, the mixture is incubated in the presence of the reducing agent for about 10 minutes or longer. In some embodiments, the mixture is incubated in the presence of the reducing agent from about 10 minutes to about 30 hours. In some embodiments, the mixture is incubated in the presence of the reducing agent from about 10 minutes to about 24 hours. In some embodiments, the mixture is incubated in the presence of the reducing agent for about 15 minutes. In some embodiments, the mixture is incubated in the presence of the reducing agent for about 20 minutes. In some embodiments, the mixture is incubated in the presence of the reducing agent for about 30 minutes. In some embodiments, the mixture is incubated in the presence of the reducing agent for about 40 minutes. In some embodiments, the mixture is incubated in the presence of the reducing agent for about 50 minutes. In some embodiments, the mixture is incubated in the presence of the reducing agent for about 1 hour. In some embodiments, the mixture is incubated in the presence of the reducing agent for about 2 hours. In some embodiments, the mixture is incubated in the presence of the reducing agent for about 3 hours. In some embodiments, the mixture is incubated in the presence of the reducing agent for about 4 hours. In some embodiments, the mixture is incubated in the presence of the reducing agent for about 4 hours. In some embodiments, the mixture is incubated in the presence of the reducing agent for about 5 hours. In some embodiments, the mixture is incubated in the presence of the reducing agent for about 6 hours. In some embodiments, the mixture is incubated in the presence of the reducing agent for about 7 hours. In some embodiments, the mixture is incubated in the presence of the reducing agent for about 8 hours. In some embodiments, the mixture is incubated in the presence of the reducing agent for about 9 hours. In some embodiments, the mixture is incubated in the presence of the reducing agent for about 10 hours. In some embodiments, the mixture is incubated in the presence of the reducing agent for about 11 hours. In some embodiments, the mixture is incubated in the presence of the reducing agent for about 12 hours. In some embodiments, the mixture is incubated in the presence of the reducing agent for about 13 hours. In some embodiments, the mixture is incubated in the presence of the reducing agent for about 14 hours. In some embodiments, the mixture is incubated in the presence of the reducing agent for about 15 hours. In some embodiments, the mixture is incubated in the presence of the reducing agent for about 16 hours. In some embodiments, the mixture is incubated in the presence of the reducing agent for about 17 hours. In some embodiments, the mixture is incubated in the presence of the reducing agent for about 18 hours. In some embodiments, the mixture is incubated in the presence of the reducing agent for about 19 hours. In some embodiments, the mixture is incubated in the presence of the reducing agent for about 20 hours. In some embodiments, the mixture is incubated in the presence of the reducing agent for about 21 hours. In some embodiments, the mixture is incubated in the presence of the reducing agent for about 22 hours. In some embodiments, the mixture is incubated in the presence of the reducing agent for about 23 hours. In some embodiments, the mixture is incubated in the presence of the reducing agent for about 24 hours. In some embodiments, the mixture is incubated in the presence of the reducing agent for about 25 hours. In some embodiments, the mixture is incubated in the presence of the reducing agent for about 26 hours. In some embodiments, the mixture is incubated in the presence of the reducing agent for about 27 hours. In some embodiments, the mixture is incubated in the presence of the reducing agent for about 28 hours. In some embodiments, the mixture is incubated in the presence of the reducing agent for about 29 hours. In some embodiments, the mixture is incubated in the presence of the reducing agent for about 30 hours.

In some embodiments, the reducing agent is 2-mercaptoethylamine (2-MEA). In some embodiments, the reducing agent is a chemical derivative of 2-MEA. In some embodiments, the reducing agent is L-cysteine. In some embodiments, the reducing agent is D-cysteine. In some embodiments, the reducing agent is glutathione. In some embodiments, the reducing agent is tris(2-carboxyethyl) phosphine.

In some embodiments, the concentration of the reducing agent in the mixture is between about 0.1 mM to about 1 M. In some embodiments, the concentration of the reducing agent in the mixture is between about 1.0 mM to about 500 mM. In some embodiments, the concentration of the reducing agent in the mixture is between about 5.0 mM to about 100 mM. In some embodiments, the concentration of the reducing agent in the mixture is about 10 mM. In some embodiments, the concentration of the reducing agent in the mixture is about 15 mM. In some embodiments, the concentration of the reducing agent in the mixture is about 20 mM. In some embodiments, the concentration of the reducing agent in the mixture is about 25 mM. In some embodiments, the concentration of the reducing agent in the mixture is about 30 mM. In some embodiments, the concentration of the reducing agent in the mixture is about 35 mM. In some embodiments, the concentration of the reducing agent in the mixture is about 40 mM. In some embodiments, the concentration of the reducing agent in the mixture is about 50 mM. In some embodiments, the concentration of the reducing agent in the mixture is about 60 mM. In some embodiments, the concentration of the reducing agent in the mixture is about 70 mM. In some embodiments, the concentration of the reducing agent in the mixture is about 80 mM. In some embodiments, the concentration of the reducing agent in the mixture is about 90 mM. In some embodiments, the concentration of the reducing agent in the mixture is about 100 mM.

In some embodiments, the concentration of 2-MEA in the mixture is between about 10 mM and about 100 mM. In some embodiments, the concentration of 2-MEA in the mixture is between about 20 mM and about 90 mM. In some embodiments, the concentration of 2-MEA in the mixture is between about 20 mM and about 80 mM. In some embodiments, the concentraton of 2-MEA in the mixture is between about 20 mM and about 70 mM. In some embodiments, the concentraton of 2-MEA in the mixture is between about 20 mM and about 60 mM. In some embodiments, the concentraton of 2-MEA in the mixture is between about 20 mM and about 50 mM. In some embodiments, the concentraton of 2-MEA in the mixture is between about 20 mM and about 40 mM. In some embodiments, the concentraton of 2-MEA in the mixture is about 20 mM. In some embodiments, the concentraton of 2-MEA in the mixture is about 25 mM. In some embodiments, the concentraton of 2-MEA in the mixture is about 30 mM. In some embodiments, the concentraton of 2-MEA in the mixture is about 35 mM. In some embodiments, the concentraton of 2-MEA in the mixture is about 40 mM.

In some embodiments the mass ratio of the total immunoglobulin in the mixture to the total reducing agent is between about 1.0 and about 5.0. In some embodiments the mass ratio of the total immunoglobulin in the mixture to the total reducing agent is between about 1.4 and about 3.8. In some embodiments the mass ratio of the total immunoglobulin in the mixture to the total reducing agent is between about 1.4 and about 3.5. In some embodiments, the mass ratio is between about 1.8 and about 3.8. In some embodiments, the mass ratio is between about 2.3 and about 3.0. In some embodiments, the mass ratio is between about 1.6 and about 2.1. In some embodiments, the mass ratio is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0. 3.1, 3.2, 3.3, 3.4, 3.5, 3.6, 3.7, 3.8, 3.9, 4.0. 4.1, 4.2, 4.3, 4.4, 4.5, 4.6, 4.7, 4.8, 4.9, or 5.0. "Mass ratio" refers to the total immunoglobulin in gram per liter to the total reducing agent in gram per liter. "Total immunoglobulin" refers to the amount of the two parental antibodies in the mixture at the beginning of the reduction step.

In some embodiments, the mixture comprises a buffer. In some embodiments, the buffer comprises a sodium acetate buffer. In some embodiments, the buffer further comprises NaCl. In some embodiments, the buffer comprises about 100 mM sodium acetate and about 30 mM NaCl. In some embodiments, pH of the buffer is about 7.3. Other buffers may be used, such as 1× Dulbecco's phosphate-buffered saline (DPBS), sodium phosphate buffer, potassium phosphate buffer, Tris buffer, histidine buffer or citrate buffer.

In some embodiments, the method further comprising a step of removing the reducing agent from the mixture.

In some embodiments, the reducing agent is removed by filtration.

In some embodiments, filtration is diafiltration.

In some embodiments, the first homodimeric antibody and the second homodimeric antibody are an IgG1, IgG2 or IgG4 isotype.

In some embodiments, the first homodimeric antibody and the second homodimeric antibody are an IgG1 isotype. In some embodiments, the first homodimeric antibody and the second homodimeric antibody are an IgG2 isotype. In some embodiments, the first homodimeric antibody and the second homodimeric antibody are an IgG4 isotype.

In some embodiments, the first CH3 domain and the second CH3 domain comprise following mutations when compared to the wild-type IgG1 of SEQ ID NO: 1, F405L/K409R, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH, Y407LWQ/K409AGRH, T366Y/F405A, T366W/F405W, F405W/Y407A, T394W/Y407T, T394S/Y407A, T366W/T394S, F405W/T394S, T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, T350V_L351Y_F405A_Y407V/T350V_T366L_K392L_T394W, K409D/D399K, K409E/D399R, K409D_K360D/D399K_E356K, K409D_K360D/D399E_E356K, K409D/D399K_E357K, K409D_K370D/D399E_E357K, K409D_K392D/D399K_E356K_E357K or K409D_K392D/ D399E_E356K_E357K. The mutations may also be introduced to the wild-type IgG2 of SEQ ID NO: 2 or wild-type IgG4 of SEQ ID NO: 3, in which case, as is well-known, the wild-type residue at the particular mutation site may not correspond to that of IgG1 due to sequence differences between wild-type IgG1, IgG2 and IgG4. For example, IgG4 mutations wild-type/F405L_R409K correspond to IgG1 mutations F405L/K409R, and IgG4 mutations R409D/D399K correspond to IgG1 mutations K409D/D399K. The mutations are compared to the reference wild-type IgG1 of SEQ ID NO: 1, IgG2 of SEQ ID NO: 2 and IgG4 of SEQ ID NO: 3.

In some embodiments, the first Fc region and/or the second Fc region comprise one or more mutations when compared to the wild-type IgG1 of SEQ ID NO: 1, wild-type IgG2 of SEQ ID NO: 2, wild-type IgG4 of SEQ ID NO: 3 that modulate binding of the first Fc region and/or the second Fc region to an Fcγ receptor (FcγR), an FcRn, or to protein A.

```
Wild-type IgG1
                                          (SEQ ID NO: 1)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

Wild-type IgG2
                                          (SEQ ID NO: 2)
ASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDK

TVERKCCVECPPCPAPPVAGPSVFLFPPKPKDTLMISRTPEVTCVVVD

VSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKN

QVSLTCLVKGFYPSDISVEWESNGQPENNYKTTPPMLDSDGSFFLYSK

LTVDKSRWQQGNVFSCSVMHEALHNHYTQKSLSLSPGK

Wild-type IgG4
                                          (SEQ ID NO: 3)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPSCPAPEFLGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RLTVDKSRWQEGNVFSCSVMHEALHNHYTQKSLSLSLGK
```

In some embodiments, the FcγR is FcγRI, FcγRIIa, FcγRIIb or FcγRIII.

In some embodiments, the one or more substitutions that modulate binding of the first Fc region and/or the second Fc region to the Fcγ are L234A_L235A, F234A_L235A, S228P_F234A_L235A, S228P_L234A_L235A, V234A_G237A_P238S_H268A_V309L_A330S_P331S, V234A_G237A, H268Q_V309L_A330S_P331S, S267E_L328F, L234F_L235E_D265A, L234A_L235A_G237A_P238S_H268A_A330S_P331S or S228P_F234A_L235A_G237A_P238S.

In some embodiments, the one or more substitutions that modulate binding of the first Fc region and/or the second Fc region to the FcRn are M428L_N434S, M252Y_S254T_T256E, T250Q_M428L, N434A and T307A_E380A_N434A, H435A, P257I_N434H, D376V_N434H, M252Y_S254T_T256E_H433K_N434F, T308P_N434A or H435R.

In some embodiments, the one or more substitutions that modulate binding of the first Fc region and/or the second Fc region to protein A are Q311R, Q311K, T307P_L309Q, T307P_V309Q, T307P_L309Q_Q311R, T307P_V309Q_Q311R, H435R or H435R_Y436F.

In some embodiments, the steps of producing the heterodimeric antibody are conducted under GMP-compliant conditions.

In some embodiments the steps of producing the heterodimeric antibody are conducted during manufacture of a drug substance comprising the heterodimeric antibody.

In some embodiments, the heterodimeric antibody is a bispecific antibody.

In some embodiments, the bispecific antibody binds CD3, BCMA or CD123.

In some embodiments, the steps of producing the heterodimeric antibody are conducted during manufacture of an innovator drug product.

In some embodiments, the steps of producing the heterodimeric antibody are conducted during manufacture of a generic drug product.

Fab-Arm Exchange and Fc Region Mutations Promoting Heterodimerization

Heterodimeric antibodies may be produced utilizing Fab-arm exchange, wherein one heavy chain and its attached light chain (half-arm) of one parental homodimeric antibody is exchanged with one heavy chain and its attached light chain of another parental homodimeric antibody to form a heterodimeric antibody composed of two heavy chains and two attached light chains (van der Neut Kolfschoten et al., (2007) *Science* 317:1554-1557).

The two homodimeric parental antibodies are engineered to have asymmetric mutations in their CH3 regions that favor Fab-arm exchange and heterodimeric antibody formation upon reduction and reformation of disulfide bridges in the hinge region of antibodies. An illustration of the Fab-arm exchange reaction is represented in FIG. 1. Upon introduction of a reducing agent into a mixture of two parental homodimeric antibodies the half-arms dissociate and the asymmetric CH3 mutations favor reformation of the heterodimeric antibodies. Subsequent reformation of the disulfide bridges between the half-arms stabilize the formed heterodimeric antibody (Gramer et al. (2013) *MAbs* 5:962-973).

In the methods of the invention any CH3 region mutation that promotes CH3 heterodimer formation may be used, such as those described herein. Several approaches are known for modifications in the CH3 region to promote heterodimerization. Typically, in all such approaches the first CH3 region and the second CH3 region are engineered in a complementary manner so that each CH3 region (or the heavy chain comprising it) can no longer homodimerize with itself but is forced to heterodimerize with the complementarily engineered other CH3 region (so that the first and second CH3 region heterodimerize and no homdimers between the two first or the two second CH3 regions are formed).

CH3 mutations that favor Fab-arm exchange include Duobody® mutations (Genmab), Knob-in-Hole mutations (Genentech), electrostatically-matched mutations (Chugai, Amgen, NovoNordisk, Oncomed), the Strand Exchange Engineered Domain body (SEEDbody) (EMD Serono), and other asymmetric mutations (e.g. Zymeworks).

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promte heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849.

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y_Y407A/T366A_K409F, L351YY407A/T366V_K409F, K392D/D399K, K392D/E356K, K253E_D282K_K322D/D239K_E240K_K292D, K392D_K409D/D356K_D399K as described in WO2007/147901, WO 2011/143545, WO2013157954, WO2013096291 and US2018/0118849.

These different approaches for Fab-arm exchange may be combined with various bispecific antibody format, such as those involving VH/VL engineering such as VH/VL domain swaps, CH1/CL domain swaps, utilizing common light chain as desrcbed in WO98050431 or utilizing tethered light chains including inside-out tethered light chains as describe in US9062120.

Further Engineering of Heterodimeric Antibodies

Fc Engineering

In addition to the CH3 region mutations that promote heterodimerization, antibodies used in the methods of the invention may comprise mutations in the Fc region that modulate antibody effector functions or half-life. Further, antibodies used in the methods of the invention may comprise Fc mutations that modulate binding of the antibodies to protein A, hence facilitating purification of the antibodies.

Fc positions that may be mutated to modulate antibody half-life (e.g. binding to FcRn include positions 250, 252, 253, 254, 256, 257, 307, 376, 380, 428, 434 and 435. Exemplary mutations that may be made singularly or in combination are mutations T250Q, M252Y, I253A, S254T, T256E, P257I, T307A, D376V, E380A, M428L, H433K, N434S, N434A, N434H, N434F, H435A and H435R. Exemplary singular or combination mutations that may be made to increase the half-life of the antibodies are mutations M428L/N434S, M252Y/S254T/T256E, T250Q/M428L, N434A and T307A/E380A/N434A. Exemplary singular or combination mutations that may be made to reduce the half-life of the antibodies are mutations H435A, P257I/N434H, D376V/N434H, M252Y/S254T/T256E/H433K/N434F, T308P/N434A and H435R.

Mutations may be introduced to the Fc region which reduce binding of the antibody to an activating Fcγ receptor (FcγR) and reduce Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the antibody to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination mutations that result in antibodies with reduced ADCC are mutations L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

Exemplary mutation that result in antibodies with reduced CDC is a K322A mutation.

Well-known S228P mutation may be made in IgG4 antibodies to enhance IgG4 stability.

Mutations may be introduced to the Fc region which enhance binding of the antibody to an Fcγ receptor (FcγR) and enhance Fc effector functions such as C1q binding, complement dependent cytotoxicity (CDC), antibody-dependent cell-mediated cytotoxicity (ADCC) and/or phagocytosis (ADCP).

Fc positions that may be mutated to increase binding of the antibody to the activating FcγR and enhance antibody effector functions include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are G236A, S239D, F243L, T256A, K290A, R292P, S298A, Y300L, V305L, K326A, A330K, I332E, E333A, K334A, A339T and P396L. Exemplary combination s that result in antibodies with increased ADCC or ADCP are a S239D/I332E, S298A/E333A/K334A, F243L/R292P/Y300L, F243L/R292P/Y300L/P396L, F243L/R292P/Y300L/V305I/P396L and G236A/S239D/I332E on IgG1.

Fc positions that may be mutated to enhance CDC of the antibody include positions 267, 268, 324, 326, 333, 345 and 430. Exemplary mutations that may be made singularly or in combination are S267E, a F1268F, S324T, K326A, K326W, E333A, E345K, E345Q, E345R, E345Y, E430S, E430F and E430T. Exemplary combination mutations that result in antibodies with increased CDC are K326A/E333A, K326W/E333A, H268F/S324T, S267E/H268F, S267E/S324T and S267E/H268F/S324T on IgG1.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells (NK), monocytes, macrophages and neutrophils via Fc gamma receptors (FcγR) expressed on effector cells. For example, NK cells express FcγRIIIa, whereas monocytes express FcγRI, FcγRII and FcγRIIIa. ADCC activity of the antibodies may be assessed using an in vitro assay using cells expressing the protein the antibody binds to as target cells and NK cells as effector cells. Cytolysis may be detected by the release of label (e.g. radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and cells that express the protein the antibody binds to as target cells also engineered to express GFP or another labeled molecule. In an exemplary assay, effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the CD11$^+$CD14$^+$ macrophages using standard methods.

"Complement-dependent cytotoxicity", or "CDC", refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate CDC by binding complement receptors (e.g., CR3) on leukocytes. CDC of cells may be measured for example by plating Daudi cells at 1×10$^5$ cells/well (50 μL/well) in RPMI-B (RPMI supplemented with 1% BSA), adding 50 μL of test antibodies to the wells at final concentration between 0-100 μg/mL, incubating the reaction for 15 min at room temperature, adding 11 μL of pooled human serum to the wells, and incubation the reaction for 45 min at 37° C. Percentage (%) lysed cells may be detected as % propidium iodide stained cells in FACS assay using standard methods.

Binding of the antibody to FcγR or FcRn may be assessed on cells engineered to express each receptor using flow cytometry. In an exemplary binding assay, 2×10$^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel, respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

"Enhance" or "enhanced" refers to enhanced effector function (e.g. ADCC, CDC and/or ADCP) or enhanced binding to an Fcγ receptor (FcγR) or FcRn of the antibody of the invention having at least one mutation in the Fc region when compared to the parental antibody without the mutation. "Enhanced" may be an enhancement of about 10%, 20%, 30%, 40%, 50%, 60%, 70%, 80%, 90%, 100% or more, or a statistically significant enhancement.

"Reduce" or "reduced" refers to reduced effector function (e.g. ADCC, CDC and/or ADCP) or reduced binding to an Fcγ receptor (FcγR) or FcRn of the antibody of the invention having at least one mutation in the Fc region when compared to the parental antibody without the mutation. "Reduced" may be a reduction of about 10%, 20%, 30%, 40%, 50%, 60%, 70%, 80%, 90%, 100% or more, or a statistically significant reduction.

"Modulate" refers to either enhanced or reduced effector function (e.g. ADCC, CDC and/or ADCP) or enhanced or reduced binding to an Fcγ receptor (FcγR) or FcRn of the antibody of the invention having at least one mutation in the Fc region when compared to the parental antibody without the mutation.

Mutations may be introduced to the antibodies used in the methods of the invention that modulate binding of the antibody to protein A. Production and purification of full length bispecific therapeutic antibodies require efficient separation of the bispecific antibodies from excess parental and/or intermediate molecules. Bispecific antibodies having protein A binding-modulating Fc mutations in asymmetric manner (e.g. in one heavy chain only) can therefore be purified from the parental antibodies based on their differential elution profile from protein A affinity columns. Exemplary mutations that may be introduced to modulate protein A binding into the antibodies used in the methods of the invention are Q311R, Q311K, T307P_L309Q, T307P_V309Q, T307P_L309Q_Q311R, T307P_V309Q_Q311R, H435R or H435R_Y436F.

Glycoengineering

The ability of the antibodies used in the methods of the invention to induce ADCC may be enhanced by engineering their oligosaccharide component. Human IgG1 is N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality, application of a variant CHO line Lec13 as the host cell line, application of a variant CHO line EB66 as the host cell line, application of a rat hybridoma cell line YB2/0 as the host cell line, introduction of small interfering RNA specifically against the α 1,6-fucosyltrasferase (FUT8) gene, or coexpression of β-1,4-N-acetylglucosaminyltransferase III and Golgi α-mannosidase II or a potent alpha-mannosidase I inhibitor, kifunensine.

The heterodimeric antibodies used in the methods of the invention may have a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

The heterodimeric antibodies used in the methods of the invention may have a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" refers to antibodies with fucose content of about 0%-15%.

"Normal fucose" or "normal fucose content" refers to antibodies with fucose content of about over 50%, typically about over 60%, 70%, 80% or over 85%.

The heterodimeric antibodies used in the methods of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the heterodimeric antibodies used in the methods of the invention may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function.

C-Terminal Lysine

The heterodimeric antibodies used in the methods of the invention may have their C-terminal lysine (CTL) partially removed during manufacturing. During manufacturing, CTL removal may be controlled to less than the maximum level by control of concentration of extracellular $Zn^{2+}$, EDTA or $EDTA-Fe^{3+}$ as described in U.S. Patent Publ. No. US20140273092. CTL content in antibodies can be measured using known methods.

The heterodimeric antibodies used in the methods of the invention may have a C-terminal lysine content of about 10% to about 90%, about 20% to about 80%, about 40% to about 70%, about 55% to about 70%, or about 60%.

The heterodimeric antibodies used in the methods of the invention may have a C-terminal lysine content of about 0%, 5%, 10%, 20%, 30%, 40%, 50%, 60%, 70%, 80%, 90% or 100%.

Antibody Allotypes

The heterodimeric antibodies used in the methods of the invention may be of any allotype. It is expected that allotype has no influence on Fab-arm exchange. Immunogenicity of therapeutic antibodies is associated with increased risk of infusion reactions and decreased duration of therapeutic response (Baert et al., (2003) *N Engl J Med* 348:602-08). The extent to which therapeutic antibodies induce an immune response in the host may be determined in part by the allotype of the antibody (Stickler et al., (2011) *Genes and Immunity* 12:213-21). Antibody allotype is related to amino acid sequence variations at specific locations in the constant region sequences of the antibody. Table 2 shows select IgG1, IgG2 and IgG4 allotypes.

TABLE 2

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n) | T | M | | | | | | |
| G2m(n-) | P | V | | | | | | |
| G2m(n)/(n-) | T | V | | | | | | |
| nG4m(a) | | | L | R | | | | |
| G1m(17) | | | | | K | E | M | A |
| G1m(17,1) | | | | | K | D | L | A |

Target Antigens

The metods of the invention may be used to generate heterodimeric antibodies with any specificity using Fab-arm exchange, as the reduction and reformation of the disulfide bonds during manufacturing is not expected to be influenced by the VH/VL regions of the antibodies, as is also demonstrated herein. The heterodimeric antibodies may bind one target antigen at two distinct epitopes, or may bind two or more target antigens, depending on the specificity of each VH/VL pair. When the heterodimeric antibody binds two target antigens, the target antigens may be located on the same cell or on two different cells. The target antigen may be a tumor-associated antigen, an antigen playing a role in inflammation, regulation of T or B cell activity, or in general any target whose biological activity is desired to be modulated, or the number of cells expressing the target are desired to be reduced.

Exemplary antigens the heterodimeric antibodies used in the methods of the invention may bind are one or more of ABCF1, ACVR1, ACVR1B, ACVR2, ACVR2B, ACVRL1, ADORA2A, Aggrecan, AGR2, AICDA, AIF1, AIG1, AKAP1, AKAP2, albumin, AMH, AMHR2, ANGPT1, ANGPT2, ANGPTL3, ANGPTL4, ANPEP, APC, APOC1, APOE, AR, AZGP1 (zinc-a-glycoprotein), B7.1, B7.2, BAD, BAFF, BAG1, BAD, BCL2, BCL6, BCMA, BDNF, BLNK, BLR1 (MDR15), BlyS, BMP1, BMP2, BMP3B (GDF10), BMP4, BMP6, BMP8, BMPR1A, BMPR1B, BMPR2, BPAG1 (plectin), BRCA1, BTLA, C19orf10 (IL27w), C3, C4A, C5, C5R1, CANT1, CASP1, CASP4, CAV1, CCBP2 (D6/JAB61), CCL1 (1-309), CCL11 (eotaxin), CCL13 (MCP-4), CCL15 (MIP-1d), CCL16 (HCC-4), CCL17 (TARC), CCL18 (PARC), CCL19 (MIP-3b), CCL2 (MCP-1), MCAF, CCL20 (MIP-3a), CCL21 (MIP-2), SLC, exodus-2, CCL22 (MDC/STC-1), CCL23 (MPIF-1), CCL24 (MPIF-2/eotaxin-2), CCL25 (TECK), CCL26 (eotaxin-3), CCL2? (CTACK/ILC), CCL28, CCL3 (MIP-1a), CCL4 (MIP-1b), CCL5 (RANTES), CCL7 (MCP-3), CCL8 (mcp-2), CCNA1, CCNA2, CCND1, CCNE1, CCNE2, CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), CD123, CD137, CD164, CD16a, CD16b, CD19, CD1C, CD20, CD200, CD-22, CD24, CD28, CD3, CDR, CD30, CD32a, CD32b, CD33, CD37, CD38, CD39, CD4, CD40, CD40L, CD44, CD45RB, CD47, CD52, CD69, CD72, CD73, CD74, CD79A, CD79B, CD8, CD80, CD81, CD83, CD86, CD89, CD96, CDH1 (E-cadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21Wap1/Cip1), CDKN1B (p27Kip1), CDKN1C, CDKN2A (p16INK4a), CDKN2B, CDKN2C, CDKN3, CEBPB, CER1, CHGA, CHGB, Chitinase, CHST10, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COL1A1, COL4A3, COL6A1, CR2, CRP, CSF1 (M-CSF), CSF2 (GM-CSF), CSF3 (GCSF), CTLA4, CTNNB1 (b-catenin), CTSB (cathepsin B), CX3CL1 (SCYD1), CX3CR1 (V28), CXCL1 (GRO1), CXCL10 (IP-10), CXCL11 (I-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYM-STR/STRL33/Bonzo), CYB5, CYC1, CYSLTR1, DAB2IP, DES, DKFZp451J0118, DNAM-1, DNCL1, DPP4, E2F1, ECGF1, EDG1, EFNA1, EFNA3, EFNB2, EGF, EGFR, ELAC2, ENG, ENO1, ENO2, ENO3, EPHB4, EPO, ERBB2 (Her-2), EREG, ERK8, ESR1, ESR2, F3 (TF), FADD, FasL, FASN, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR, FGFR3, FIGF (VEGFD), FIL1 (EPSILON), FIL1 (ZETA), FLJ12584, F1125530, FLRT1 (fibronectin), FLT1, FOS, FOSL1 (FRA-1), FY (DARC), GABRP (GABAa), GAGEB1, GAGEC1, GALNAC4S-6ST, GATA3, GDF5, GFI1, GGT1, GITR, GITRL, GM-CSF, GNAS1, GNRH1, GPR2 (CCR10), GPR31, GPR44, GPR81 (FKSG80), GRCC10 (C10), GRP, GSN (Gelsolin), GSTP1, HAVCR2, HDAC4, HDAC5, HDAC7A, HDAC9, HGF, HIF1A, HIP1, histamine and histamine receptors, HLA, HLA-A, HLA-DRA, HM74, HMOX1, HUMCYT2A, HVEM, ICEBERG, ICOS, ICOSL, IDO, ID2, IFN-a, IFNA1, IFNA2, IFNA4, IFNA5, IFNA6, IFNA7, IFNB1, IFNgamma, IFNW1, IGBP1, IGF1, IGF1R, IGF2, IGFBP2, IGFBP3, IGFBP6, IL-1, IL10, IL10RA, IL10RB, IL11, IL11RA, IL-12, IL12A, IL12B, IL12RB1, IL12RB2, IL13, IL13RA1, IL13RA2, IL14, IL15, IL15RA, IL16, IL17, IL17B, IL17C, IL17R, IL18, IL18BP, IL18R1, IL18RAP, IL19, IL1A, IL1B, IL1F10, IL1F5, IL1F6, IL1F7, IL1F8, IL1F9, IL1HY1, IL1R1, IL1R2, IL1RAP, IL1RAPL1, IL1RAPL2, IL1RL1, IL1RL2, IL1RN, IL2, IL20, IL20RA, IL21R, IL22, IL22R, IL22RA2, IL23, IL24, IL25, IL26, IL27, IL28A, IL28B, IL29, IL2RA, IL2RB, IL2RG, IL3, IL30, IL3RA, IL4, IL4R, IL5, IL5RA, IL6, IL6R, IL6ST (glycoprotein 130), IL7, IL7R, IL8, IL8RA, IL8RB, IL8RB, IL9, IL9R, ILK, INHA, INHBA, INSL3, INSL4, insulin, insulin receptor, IRAK1, IRAK2, ITGA1, ITGA2, ITGA3, ITGA6 (a6 integrin), ITGAV, ITGB3, ITGB4 (b 4 integrin), JAG1, JAK1, JAK3, JUN, K6HF, KAI1, KDR, KITLG, KIR, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAG-3, LAMA5, LDL, LEP (leptin), LFA, Lingo-p75, Lingo-Troy, LPS, LTA (TNF-b), LTB, LTB4R (GPR16), LTB4R2, LTBR, MACMARCKS, MAG or Omgp, MAP2K7 (c-Jun), MDK, mesothelin, c-Met, MIB1, midkine, MIF, MIP-2, MKI67 (Ki-67), MMP2, MMP9, MS4A1, MSMB, MT3 (metallothionectin-III), MTSS1, MUC1 (mucin), c-MYC, MYD88, NCK2, neurocan, NFKB1, NFKB2, NGFB (NGF), NGFR, NgR-Lingo, NgR-Nogo66 (Nogo), NgR-p75, NgR-Troy, NKG2D, NKp46, NME1 (NM23A), NOX5, NPPB, NR0B1, NR0B2, NR1D1, NR1D2, NR1H2, NR1H3, NR1H4, NRII2, NRII3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZ1, OPRD1, OX-40, OX-40L, P2RX7, PAP, PART1, PATE, PAWR, PCA3, PCNA, PD-1, PD-L1, PDGFA, PDGFB, PECAM1, PF4 (CXCL4), PGF, PGR, phosphacan, PIAS2, PIK3CG, PLAU (uPA), PLG, PLXDC1, PPBP (CXCL7), PPID, PRI, PRKCQ, PRKD1, PRL, PROC, PROK2, PSAP, PSCA, PSMA, PTAFR, PTEN, PTGS2 (COX-2), PTN, RAC2 (p21Rac2), RARB, RGS1, RGS13, RGS3, RNF110 (ZNF144), ROBO2, ROR1, SI00A2, SCGB1D2 (lipophilin B), SCGB2A1 (mammaglobin 2), SCGB2A2 (mammaglobin 1), SCYE1 (endothelial Monocyte-activating cytokine), SDF2, SERPINA1, SERPINA3, SERPINB5 (maspin), SERPINE1 (PAI-1), SERPINF1, SHBG, SLA2, SLC2A2, SLC33A1, SLC43A1, SLIT2, SPP1, SPRR1B (Spr1), ST6GAL1, STAB1, STAT6, STEAP, STEAP2, TB4R2, TBX21, TCP10, TDGF1, TEK, TF (transferrin receptor), TGFA, TGFB1, TGFB111, TGFB2, TGFB3, TGFBI, TGFBR1, TGFBR2, TGFBR3, TH1L, THBS1 (thrombospondin-1), THBS2, THBS4, THPO, TIE (Tie-1), TIGIT, TIM-3, TIMP3, tissue factor, TLR10, TLR2, TLR3, TLR4, TLR5, TLR6, TLR7, TLR8, TLR9, TNF, TNF-a, TNFAIP2 (B94), TNFAIP3, TNFRSF11A, TNFRSF1A, TNFRSF1B, TNFRSF21, TNFRSF5, TNFRSF6 (Fas), TNFRSF7, TNFRSF8, TNFRSF9, TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Iia), TP53, TPM1, TPM2, TRADD, TRAF1, TRAF2, TRAF3, TRAF4, TRAF5, TRAF6, TREM1, TREM2, TRPC6, TSLP, TWEAK, VEGF, VEGFB, VEGFC, versican, VHL C5, VISTA, VLA-4, XCL1 (lymphotactin), XCL2 (SCM-1b), XCR1 (GPR5/CCXCR1), YY1, and ZFPM2.

In some embodiments, the heterodimeric antibody used in the methods of the invention binds CD3.

In some embodiments, the heterodimeric antibody used in the methods of the invention binds CD3 and a tumor-associated antigen (TAA).

In some embodiments, the heterodimeric antibody used in the methods of the invention binds CD123 and CD3 and BCMA and CD3.

In some embodiments, the heterodimeric antibody used in the methods of the invention binds EGFR and c-Met.

In some embodiments, the heterodimeric antibody that binds EGFR and c-Met comprises a first heavy chain (HC1) of SEQ ID NO: 4, a first light chain (LC1) of SEQ ID NO: 5, a second heavy chain (HC2) of SEQ ID NO: 6 and a second light chain (LC2) of SEQ ID NO: 7.

The invention also provides a bispecific antibody produced by the methods of the invention.

The invention also provides a bispecific antibody that binds EGFR and c-Met produced by the methods of the invention.

The invention also provides a bispecific antibody that binds EGFR and c-Met comprising a first heavy chain (HC1) of SEQ ID NO: 4, a first light chain (LC1) of SEQ ID NO: 5, a second heavy chain (HC2) of SEQ ID NO: 6 and a second light chain (LC2) of SEQ ID NO: 7 produced by the methods of the invention.

Production of Homodimeric and Heterodimeric Antibodies

The first homodimeric antibody and the second homodimeric antibody may be produced together or separately in a culture vessel such as bioreactor. The first homodimeric antibody and the second homodimeric antibody may be produced by expression in a host cell by co-expression or by using a separate host cell to produce each homodimeric antibody. In the latter case the host cell may be of same or different origin.

"Host cell" refers to a cell into which one or more vectors has been introduced which express at least one antibody heavy chain and one antibody light chain "Host cell" refers not only to the particular subject cell but to the progeny of such a cell, and also to a stable cell line generated from the particular subject cell. Because certain modifications may occur in succeeding generations due to either mutation or environmental influences, such progeny may not be identical to the parent cell but are still included within the scope of the term "host cell" as used herein.

Such host cells may be eukaryotic cells, prokaryotic cells, plant cells or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (for example, *S. cerevisiae*) and Pichia are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHOK1SV (Lonza Biologics, Walkersville, MD), Potelligent® CHOK2SV (Lonza), CHO-K1 (ATCC CRL-61) or DG44.

Exemplary vectors that may be used to express one or more antibody heavy chains and light chains include pWLneo, pSV2cat, pOG44, PXR1, pSG (Stratagene) pSVK3, pBPV, pMSG and pSVL (Pharmacia), pEE6.4 (Lonza) and pEE12.4 (Lonza) as well as vectors used in Lonza Xceed system.

The first homodimeric antibody and the second homodimeric antibody may be produced by expressing them in a separate host cell. In this case, the first homodimeric antibody and the second homodimeric antibody may be purified piror to mixing them in the presence of a reducing agent to initiate the Fab-arm exchange. Purification may be accomplished using known methods such as protein A chromatography. Alternatively, culture media containing the first homodimeric antibody and the second homodimeric antibody may be combined into which a reducing agent may be added to initiate the Fab-arm exchange. If the first homodimeric antibody and the second homodimeric antibody are produced by co-expression, the antibodies may also be purified using protein A chromatography.

The Fab-arm exchange to generate heterodimeric antibodies is described herein. Process conditions such as concentration of the first homodimeric antibody and the second homodimeric antibody, reducing agent, concentration off the reducing agent, time of reduction, concentration of dissolved oxygen, temperature in which the reaction is conducted and buffers used are optimized to produce heterodimeric antibodies with high yield and purity as described herein.

After Fab-arm exchange, the produced heterodimeric antibody may be further purified. Methods for purification include combination of protein A, protein G chromatography, other ways of affinity chromatography, such as affinity chromatography based on antigen binding or binding to anti-idiotypic antibodies, thioaffinity, ionic exchange, hydrophobic interaction, hydroxyapaptite chromatography and other mixed mode resins. Additional methods may use precipitation with for example salts or polyethylene glycol to obtained purified heterodimeric antibodies.

Equipment suitable for the process of the method of the present invention are known. Expression of homodimeric antibodies by a host cell may for example typically be performed in a reaction vessel, such as a bioreactor. The reducing and oxidizing steps may take place in the same bioreactor as expression of the first homodimeric antibody and/or the second homodimeric antibody or it may take place in separate reactor vessel. The reaction vessel and supporting process piping may be disposable or re-usable and made from standard materials (plastic, glass, stainless steel etc). The reaction vessel may be equipped with mixing, sparging, headspace gassing, temperature control and/or be monitored with probes for measurement of temperature, weight/volume, pH, dissolved oxygen (DO), and redox potential. All such techniques are common within standard unit operations of a manufacturing plant and well known to a person skilled in the art.

While having described the invention in general terms, the embodiments of the invention will be further disclosed in the following examples that should not be construed as limiting the scope of the claims.

Example 1

General Methods cSDS

Capillary sodium dodecyl sulfate-polyacrylamide gel electrophoresis separates proteins on the basis of molecular weight. Analysis employed a commercial capillary electrophoresis system with a fused silica capillary in a temperature-controlled cartridge. The test articles were mixed with internal standards and alkylating reagent, heated for a defined time and temperature to denature the protein. Samples were then injected electro-kinetically by voltage and then analyzed by application of a greater electric field for a predefined duration. Detection was accomplished by absorbance at 220 nm and purity determined by calculating the corrected peak area of the main peak relative to all other peaks in the electrophoregram after the internal standard.

IEX-HPLC

Percent bispecific antibody in relation to residual parental homodimers antibodies were determined by Ion Exchange High Performance Liquid Chromatography (IEX-HPLC). Ion exchange chromatography achieves separation by exploting differences in the surface charge on the molecules. IEX-HPLC was performed using Thermo Scientific, Propac WCX-10, (4 mm ID×150 mm, packed 10 um particles). Seperation of species were resolved using a salt gradient and/or a pH gradient. As the gradient concentration increased, the overall surface interaction of each antibody with the column is neutralized and elution is detected at 280 nm. The relative amount of each IgG was measured by comparing peak area count.

HIC-HPLC

Hydrophobic interaction chromatography method to separate proteins based on their hydrophobic nature. Proteins are retained on the column under high salt conditions and are eluted by decreasing the salt concentration. High salt buffer conditions expose the hydrophobic regions due to decreased solvation of the protein and promotes binding to the HIC stationary phase. Samples were injected onto a Tosoh TSK-gel Butyl-NPR (4.6 mm×10 cm, 2.5 um non-porous resin based bead) column and eluted with a ammonium sulfate gradient. The absorbance monitored at 280 nm and peaks identified compared to reference standard injections.

RP-HPLC (To Detect Cystamine)

Reverse Phased High Performance Chromatography separates solute molecule in the mobile phase based the hydrophobic binding interactions to the stationary phase media. The differences in hydrophobicity of the 2-MEA and oxidized dimeric form cystamine were exploited to resolve and quantitate by RP-HPLC by comparing measured values to standard curves. A Phenomenex Luna 18 (4.6 mm×150 mm, 3 um) column using a hexane sulfonate/acetonitrile moble phase system was used to separate the two species with step gradients of increasing organic solvent. The species were detected by monitoring absorbance at 220 nm (2-MEA) and 255 nm (cystamine) and the peak areas compared to their relative standard curves.

General Antibody Production Scheme for Mono and Bispecific (The One Done at 200 ml Scale) and Scale Each monospecific antibody was thawed from individual mammalian cell banks, expanded, and expressed separately in bioreactors. The production bioreactors were supplemented with enriched medias and harvested prior to significant cell death. The bioreactors were harvested by means of centrifugation and/or filtration, and the monospecific antibodies were captured separately by affinity protein A chromatrography. The resulting captured monospecific antibodies were then stored frozen until combined in the FAE stage.

Example 2

Process Improvements During Manufacturing of Bispecific Antibodies Using Fab-Arm Exchange Bispecific antibodies were generated using Fab-arm exchange by introduction of asymmetrical mutations in the CH3 domain of the two homodimer parental antibodies followed by reduction and reformation of intermolecular disulfide bonds. The asymmetric CH3 domain mutations drive preferential formation of the heterodimeric bispecific antibody over the homodimeric parental antibodies.

To ensure process robustness during manufacturing, experiments were designed to gain understanding of possible thresholds and ranges for various parameters during manufacturing. Antibody disulfide bond reformation has been shown to be dependent on the presence of oxygen and free metals, as EDTA and oxygen-free conditions inhibited re-oxidation of cysteines in an antibody to disulfide bonds (US2014/0303356). Hence studies were initiated to investigate the necessity to control the amount of dissolved oxygen ($DO_2$) and metals during manufacturing of bispecific antibodies utilizing Fab-arm exchange.

Figure 2:
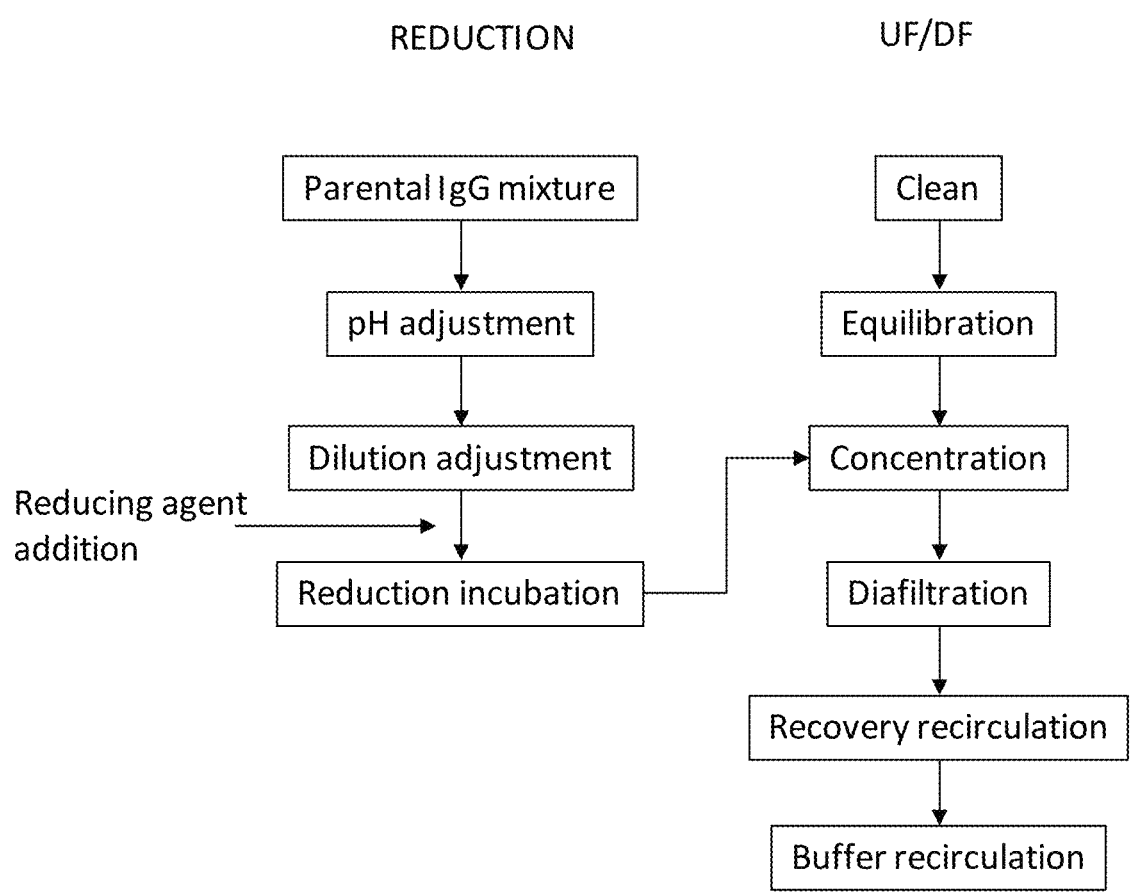
FIG. 2 shows process steps during reduction and ultrafiltration/diafiltration (UF/DF) during manufacturing of bispecific antibodies using Fab-arm exchange.

FIG. 2 shows the manufacturing steps during reduction and reformation of the disulfide bonds during manufacturing of bispecific antibodies by Fab-arm exchange.

Figure 3:
FIG. 3 shows molecular details of the thiol-disulfide exchange reactions

In theory, antibody disulfide bond reformation after reduction with a reducing agent such as 2-Mercaptoethylamine (2-MEA) may occur via various routes. For example, thiol-disulfide exchange may account for the reduction and reformation of the disulfide bonds. In order for the thiol-disulfide exchange to proceed, the reducing agent such as 2-MEA needs to be in its thiolate ($RS^-$) form for the thiol-disulfide exchange to proceed. FIG. 3 shows the molecular details of the thiol-disulfide exchange reaction. To reduce the disulfide bonds in the parental antibodies, the thiolate anion (circled in the FIG. 3) attacks the sulfur atom of the disulfide bond, displacing one of the sulfur atom and forming a new disulfide bond with the 2-MEA thiolate.

Using the Henderson-Hasselbalch equation shown below, the ratio of the 2-MEA thiol (SH) and thiolate anion ($S^-$) is highly dependent on the pH and 2-MEA thiol $pK_a$.

$$\frac{[S^-]}{[SH]} = 10^{(pH-pK_a)}$$

Hence, the reduction of dilsulfide bonds and overall Fab-arm exchange becomes inhibited at low pH, where the protonated thiol form of 2-MEA is favored relative to its deprotonated thiolate anion form. At higher pH, the equilibrium shifts towards thiolates enabling the reduction of disulfide bonds and thiol-disulfide exchange.

Figure 4:
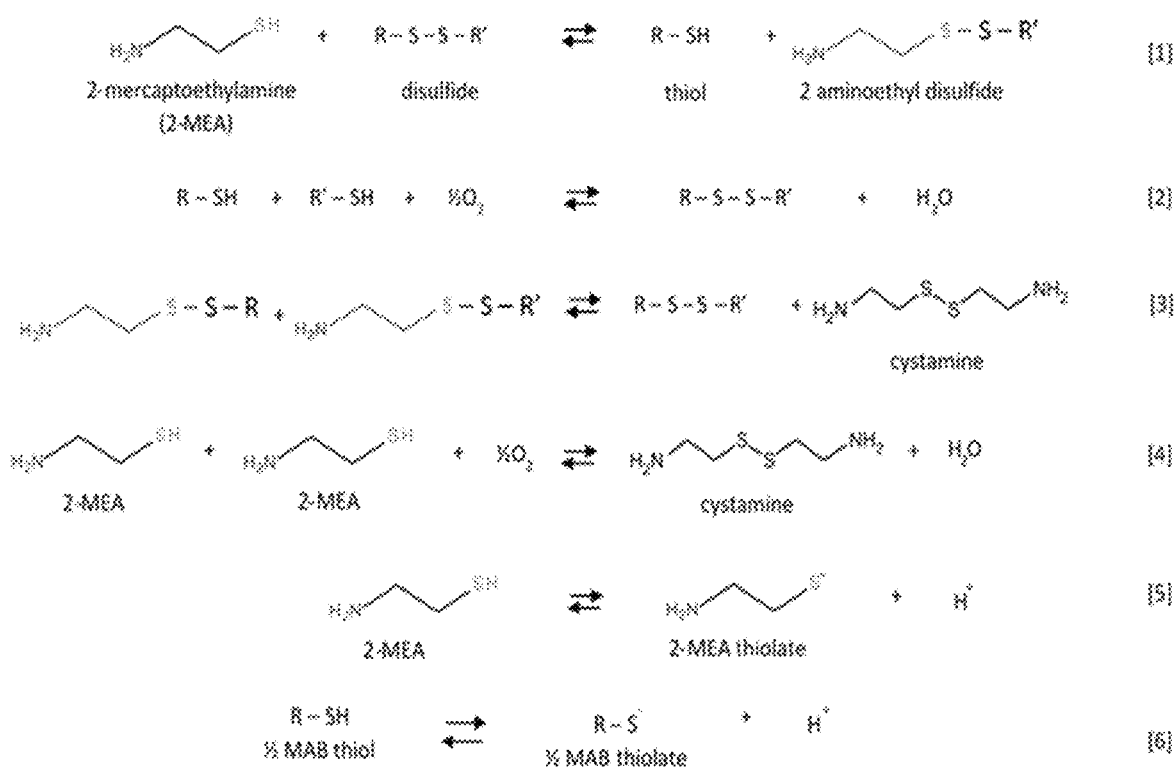
FIG. 4 shows a summary of the reactions that may take place during Fab-arm exchange in the presence of 2-MEA.

A summary of the reactions that may take place during Fab-arm exchange in the presence of 2-MEA is presented in FIG. 4. During Fab-arm exchange, the removal of a reducing agent such as 2-MEA by buffer exchange (during UF/DF) enables the reformation of disulfide bonds in the heterodimer bispecific antibody, however multiple reaction pathways allow for the disulfide reformation process to occur. In the presence of oxygen, the oxygen may react with protonated thiolates facilitating reformation of the disulfide bonds in the heterodimeric bispecific antibody as illustrated by Reaction 2 in FIG. 4. The presence of oxygen may also deplete the residual 2-MEA thiols in solution forming a cystamine dimer and water as shown by Reaction 4 in FIG. 4. Thus, sufficiently high concentration of 2-MEA should be used during the Fab-arm exchange to improve efficiency and yield of the bispecific antibody.

However, thiolate disulfide exchange and reformation of disulfide bonds may still be possible in the absence of oxygen. Under oxygen deprived conditions, as the concentration of 2-MEA decreases during the buffer exchange process, antibody thiol groups and 2-aminoethyl disulfide Fab intermediate may drive Reaction 1 of FIG. 4 in the reverse direction reforming the disulfide bonds in the bispecific heterodimeric antibodies with concomitant production of 2-MEA thiolate. This reaction would continue to be pushed into the reverse direction as more 2-MEA is removed during the buffer exchange process.

Example 3

Bispecific Antibody A Manufacturing in Low $DO_2$ Conditions During UF/DF

Experimental Method

In this experiment, ambient $DO_2$ leves were present during reduction and up to 23 hours post-2-MEA addition, after which a nitrogen overlay was included to minimize % $DO_2$ during UF/DF. The approach reflected conditions in which oxygen was present during the reduction phase and absent during reformation of the disulfide bonds.

Bispecific antibody A binds BCMA and CD3 and is an IgG4 isotype with S228P, F234A, L235A substitutions ("PAA substitutions") in both heavy chains, F at position 405 and R at postion 409 in one heavy chain and L at positon 405 and K at position 409 in the second heavy chain to drive heterodimer formation. The parental antibodies were named p1A-IgG4PAAF405R409 and p2A-IgG4PAAL405K409.

Parental antibodies p1A-IgG4PAAF405R409 and p2A-IgG4PAAL405K409 were harvested from cell culture bioreactors and purified by protein A affinity chromatography.

A solution was prepared using p1A-IgG4PAAF405R409 and p2A-IgG4PAAL405K409 at a steered molar ratio or 1:1.06 to intentional limit one of the parantal antibodies. The mixture was then adjusted to pH 7.3 and diluted to a total IgG concentration of 10.5 g/L using 101 mM sodium acetate, 105 mM Tris Base, pH 7.3. A 50 mM Sodium Acetate, 800 mM 2-MEA pH 5.0 stock solution was added to the parental mAb mixture. The final reduction buffer composition piror to UF/DF was about 100 mM sodium acetate, about 35 mM 2-MEA, about 30 mM NaCl, pH 7.3. The reduced parental mAb solution was incubated for 23 hrs at 24° C. and subsequently transferred to the UF/DF retentate vessel. Prior to the start of ultrafiltration (UF) and diafiltration (DF), an overlay of nitrogen was delivered to the retentate vessel via the headspace of the vessel to depelete $DO_2$ during reformation of the disculfide bridges and was maintained throughout the entirety of the UF and DF process. To prevent the addition of $DO_2$ through the diafiltration buffer, the diafiltration buffer (100 mM Tris-acetate 30 mM NaCl pH 7.5) was sparged with nitrogen throughout processing. In-line $DO_2$ sensors were used to verify that the retentate $DO_2$ had reached levels below 5% $DO_2$ and the diafiltration buffer had reached levels below 1% $DO_2$ prior to the start of the UF and DF steps.

Throughout the UF and DF process, the $DO_2$ levels were measured in the feed inlet, retentate, and permeate lines during the UF/DF and were all maintained at <4% $DO_2$. The diafiltration buffer was maintained at levels <1% $DO_2$. The UF/DF system was maintained at a 54 mL/min crossflow rate, targeting a transmembrane pressure of 14.5 psi for 11 diafiltration volumes (DV). All processes following the incubation were performed at room temperature (18-22° C.). Upon completion of UF/DF, the recovered retentate was quenched with 1.0 M Acetic Acid and adjusted to pH 5.0 to minimize further disulfide bond formation and subsequently stored at 2-8° C. No additional buffer recovery flush was performed following the completion of UF/DF to prevent any possible oxidation of the material from the introduction of the additional diafiltration buffer.

Figure 5:
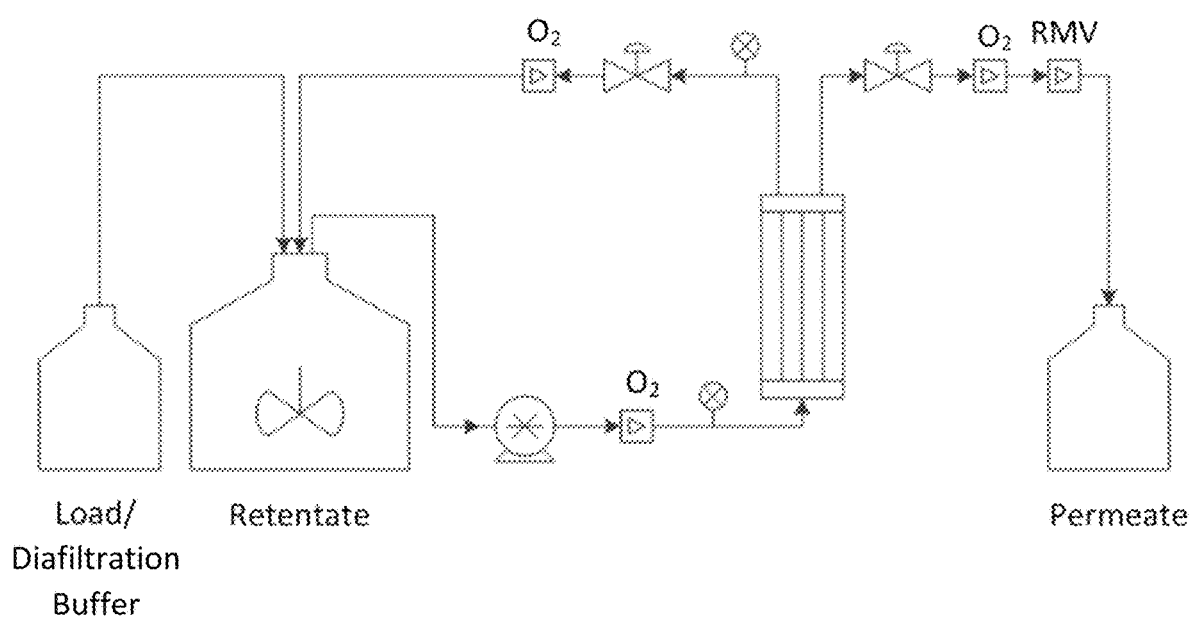
FIG. 5 shows a cartoon of the UF/DF setup and the location of $DO_2$ and pH sensors where RmV=relative millivolts.

The UF/DF setup was equipped to measure $DO_2$ at 3 locations while processing. In line monitoring of % $DO_2$ in the feed inlet, retentate, and permeate lines is shown in FIG. 5. Upon lowering the $DO_2$, the levels remained below 5% in the permeate and below 3% in the inlet/retentate. Table 3 shows the summary of UF/DF process parameters and performance.

TABLE 3

| | |
|---|---|
| Final 2-MEA Concentration (mM) | 35.0 |
| TMP (psi) | 14.5-16.0 |
| Crossflow (mL/min) | 53-55 |
| Diafiltration Concentration (g/L) | 25.0 |
| Total Diafiltration Volumes (DVs) | 11 |
| Mean Permeate Flux (L/m2/hr) | 23.2 |
| Load ratio (g/m2) | 320 |
| Yield (%) | 88 |

Figure 6:
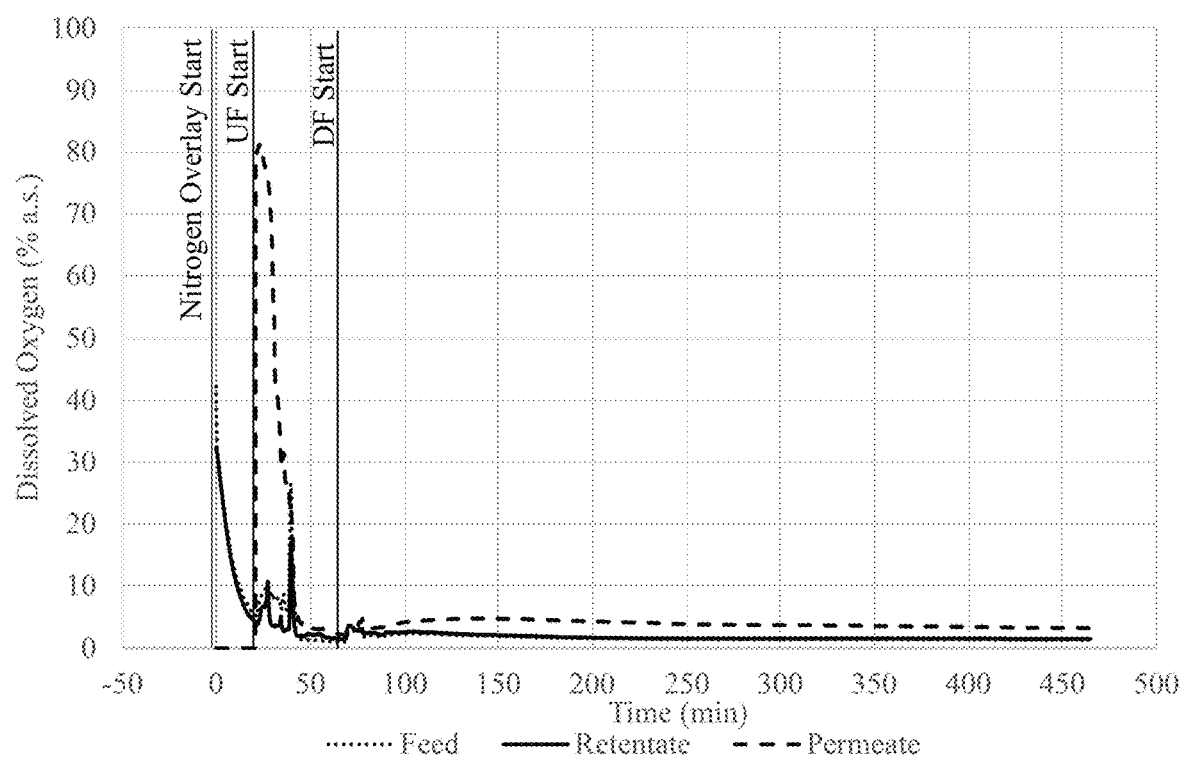
FIG. 6 shows percent (%) $DO_2$ during UF/DF measured in the retentate, permeate and inlet lines during manufacturing of bispecific antibody A in low $DO_2$ conditions during UF/DF. a.s.: air saturated.

Table 4 shows the summary of offline % $DO_2$, pH and conductivity measurements during pre- and post 2-MEA addition. FIG. 6 shows the percent (%) $DO_2$ during UF/DF measured in the retentate, permeate and inlet lines. The % $DO_2$ stabilized to 3.2% in the permeate, 1.5% in the retentate and 1.4% in the feed over time after nitrogen overlay in retentate in recirculation.

Non-reduced cSDS analysis was used to measure disulfide bond integrity of the formed heterodimeric bispecific antibody (measured as % purity of the heterodimeric antibody on non-reduced cSDS). The purity of antibody A was measured to be 97.59%.

This study demonstrated that under ambient % $DO_2$ (ranging from 89-13%) during reduction and a low % $DO_2$ environment (<4% $DO_2$ during the UF/DF) the bispecific antibody A formed with high levels of disulfide bond formation (reflected by % purity on non-reduced cSDS). Previously, it was believed that $DO_2$ would be required to oxidize thiols into disulfide bonds to stabilize the bispecific antibody.

TABLE 4

| Step | Dissolved Oxygen (%) | pH | Conductivity (mS/cm) |
|---|---|---|---|
| Parental IgG mixture | 88.1 | 4.99 | 3.37 |
| pH Adjusted Parental Pool | 87.5 | 7.35 | 4.43 |
| Diluted pH Adjusted Parental Pool | 88.9 | 7.33 | 4.39 |
| Post 2-MEA Addition (T = 0) | 36.9 | 6.99 | 7.73 |
| Post 2-MEA Addition (T = 2 hr) | 18.7 | | |
| Post 2-MEA Addition (T = 23 hr) | 13.2 | | |

The levels of oxygen present during this study was calculated not to be sufficient to contribute to oxidation of the thiols during UF/DF. The calculation below demonstrated that $DO_2$ concentration above 30% in solution was needed for oxidation of thiols to occur using the reaction represented by Reaction 2 in FIG. 4.

For this study, the following assumptions were made to calculcate theoretical percentage $DO_2$ saturated solution to oxidize all thiols in the amount of antibody present:

IgG solution: 10 g/L
moles S—S (disulfide bonds to be reduced and oxidized)/mole mAb
½ mole $O_2$/mole S—S If oxygen is required to generate disulfide bonds from thiols, refer to Reaction 2 of FIG. 4
Oxygen solubility in air saturated water=7 ppm (g $O_2$/106 g solution)=100% saturation
mAb MW: 150 kDa To calculate % dissolved $DO_2$ concentration to oxidize 10 mg/mL antibody solution when 4 disulfides/mole mAb is oxizide and $O_2$ required to oxidize all thiols:

1. (10 mg mAb/mL solution)*(mole mAb/150000 g mAb) *(2 moles S—S/mole mAb)*(½ mole $O_2$/mole S—S) *(1000 mL/1 L) (1 g/1000 mg)=$6.67 \times 10^{-4}$ moles $O_2$/L solution
2. ($6.67 \times 10^{-5}$ moles $O_2$/L solution)*(31.998 g $O_2$/1 mole $O_2$)*(1 L/1000 g)=$2.13 \times 10^{-6}$ g $O_2$/g solution
3. ($2.13 \times 10^{-6}$ g $O_2$/g solution)*($10^6$ g solution)=2.13 g $O_2/10^6$ g solution=2.13 ppm
4. Air saturated water about 7 g $O_2/10^6$ g solution=7 ppm
5. 2.13 ppm/7 ppm=30% $O_2$ saturated solution needed 2% $DO_2$ at operating temperatures was equivalent to 0.192 mg/L or 6.00 µM, 3% $DO_2$ was equivalent to 0.288 mg/L or 8.99 µM, 4% $DO_2$ was equivalent to 0.384 mg/L or 11.29 µM, 5% $DO_2$ was equivalent to 0.480 mg/L or 14.99 µM. 30% $DO_2$ was equivalent to 2.88 mg/L or 90 µM.

This indicates that oxygen independent chemical reaction pathways existed that allowed reformation of the disulfide bonds in the absence of oxygen during the UF/DF step. It is possible that as 2-MEA is removed from solution the reverse reaction of Reaction 1 of FIG. 4 is driving the reformation of the disulfide bridges in the heterodimeric bispecific antibody.

Conclusion: Maintaining levels of $DO_2$ at <4% during UF/DF did not significantly affect disulfide bond formation. At completion of the UF/DF, purity of the bispecific antibody was >97%.

Example 4

Bispecific Antibody B Manufacturing in Low $DO_2$ During UF/DF

In this experiment, ambient $DO_2$ leves were present during reduction and up to 23 hours post-2-MEA addition, after which a nitrogen overlay was included to minimize % $DO_2$ during UF/DF. The approach reflected conditions in which oxygen was present during the reduction phase and absent during reformation of the disulfide bonds.

Bispecific antibody B binds CD123 and CD3 and is an IgG4 isotype with S228P, F234A, L235A substitutions ("PAA substitutions") in both heavy chains, F at position 405 and R at postion 409 in one heavy chain and L at positon 405 and K at position 409 in the second heavy chain to drive heterodimer formation. The parental antibodies were named p1B-IgG4PAAF405R409 and p2B-IgG4PAAL405K409.

The parental antibodies p1B-IgG4PAAF405R409 and p2B-IgG4PAAL405K409 were harvested from cell culture bioreactors and purified by protein A affinity chromatography.

A solution of p1B-IgG4PAAF405R409 and p2B-IgG4PAAL405K409 was prepared and adjusted to pH 7.3 and diluted to a total IgG concentration of 10.5 g/L using 101 mM sodium acetate, 105 mM Tris Base, pH 7.3. A 50 mM Sodium Acetate, 800 mM 2-MEA pH 5.0 stock solution was added to the parental mixture. The final reduction buffer composition piror to UF/DF was about 100 mM sodium acetate, about 35 mM 2-MEA, about 30 mM NaCl, pH 7.3. The reduced parental solution was incubated for 23 hrs at 24° C. and subsequently transferred to the UF/DF retentate vessel. Prior to the start of ultrafiltration (UF) and diafiltration (DF), an overlay of nitrogen was delivered to the retentate vessel via the headspace of the vessel to deplete $DO_2$ during reformation of the disulfide bridges and was maintained throughout the entirety of the UF and DF process. To prevent the addition of $DO_2$ from the diafiltration buffer, the diafiltration buffer (100 mM Tris-acetate 30 mM NaCl pH 7.5) was sparged with nitrogen throughout processing. In-line $DO_2$ sensors were used to verify that the retenate had reached levels below 5% $DO_2$ and the diafiltration buffer had reached levels below 1% prior to the start of the UF and DF steps.

Throughout the UF and DF process, the $DO_2$ levels were measured in the feed inlet, retentate, and permeate lines during the UF/DF and were all maintained at <4% $DO_2$. The diafiltration buffer was maintained at levels <1% $DO_2$. The UF/DF system was maintained at a 42 mL/min crossflow rate, targeting a transmembrane pressure of 15.0 psi for 11 diafiltration volumes (DV). All processes following the incubation were performed at room temperature (18-22° C.). Upon completion of UF/DF, a 3 mL sample was taken, remained unadjusted at pH 7.5, and immediately stored at −70° C. to prevent further oxidation. The remaining bulk of recovered retentate was quenched with 1.0 M Acetic Acid and adjusted to pH 5.0, to minimize further disulfide bond formation. The bulk material was subsequently stored at −70° C. No additional buffer recovery flush was performed following the completion of UF/DF to prevent any possible oxidation of the material from the introduction of the additional diafiltration buffer, however yields were lower than typically observed.

The UF/DF setup was equipped to measure $DO_2$ at 3 locations while processing. In line monitoring of % $DO_2$ in the feed inlet, retentate, and permeate lines is shown in FIG. 5. Upon lowering the $DO_2$, the levels remained below 5% in the permeate and below 3% in the inlet/retentate.

Figure 7:
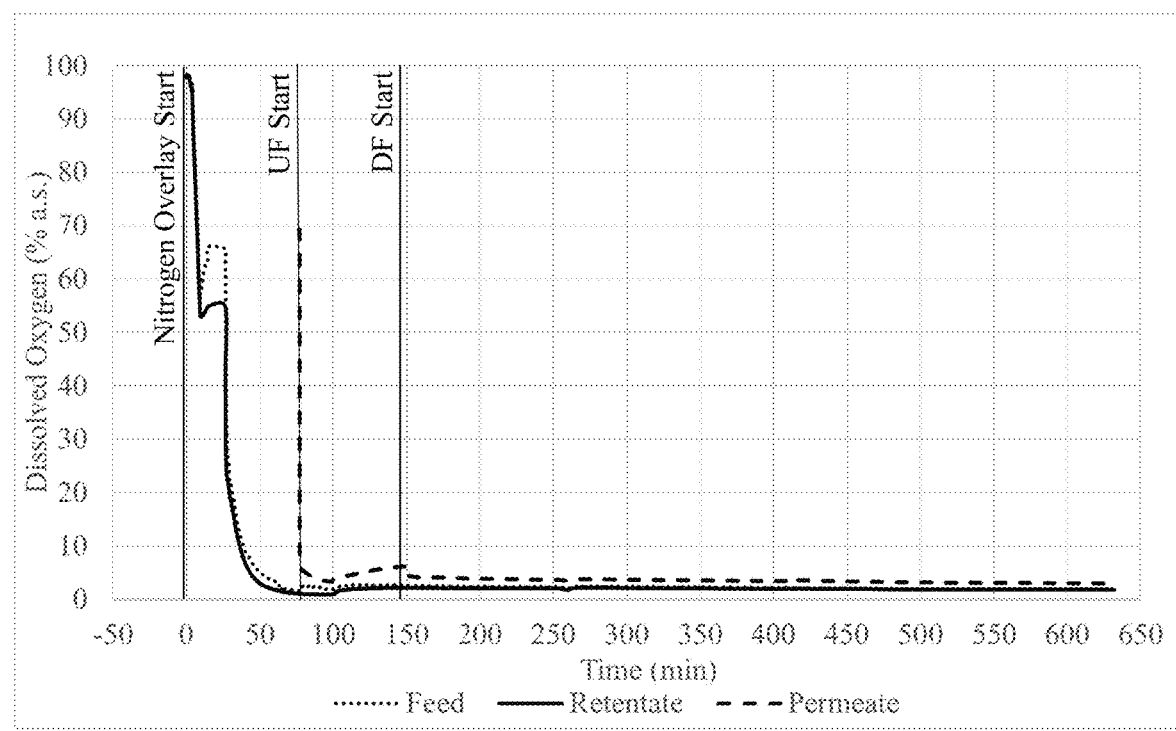
FIG. 7 shows percent (%) $DO_2$ during UF/DF measured in the retentate, permeate and inlet lines during manufacturing of bispecific antibody B in low $DO_2$ conditions during UF/DF. a.s.: air saturated.

Table 5 shows the summary of UF/DF procses parameters. FIG. 7 shows the % $DO_2$ during UF/DF measured in the retentate, permeate and inlet inles. Table 6 shows the summary of offline % $DO_2$, pH and conductivity measurements.

TABLE 5

| | |
|---|---|
| Final 2-MEA Concentration (mM) | 35.0 |
| TMP (psi) | 15.0-16.5 |
| Crossflow (mL/min) | 42-45 |
| Diafiltration Concentration (g/L) | 25.0 |
| Total Diafiltration Volumes (DVs) | 11 |
| Mean Permeate Flux (L/m2/hr) | 17.7 |
| Load ratio (g/m2) | 320 |
| Yield (%) | 85 |

TABLE 6

| Step | % $DO_2$ | pH | Conductivity (mS/cm) | RmV |
|---|---|---|---|---|
| Parental Pool | 82.9 | 4.61 | 2.57 | 189 |
| pH Adjusted Parental Pool | 80.3 | 7.26 | 4.55 | 106 |
| Post 2-MEA Addition (T = 0) | 78.1 | 7.22 | 7.55 | −314 |
| Post 2-MEA Addition (T = 23 hr) | 24.4 | | | |

Non-Reduced cSDS analysis was used to measure the disulfide bond integrity in the formed bispecific antibody for both the frozen samples at pH 7.5 and the bulk material at pH 5.0. Purity of the pH 7.5 bispecific antibody preparation was measured to be 97.16% and purity of the antibody preparation at pH 5.0 was measured to be 97.27%.

This study demonstrated that under ambient % $DO_2$ (ranging from 83-24%) during the Reduction and a low % $DO_2$ environment (<4% $DO_2$) during the UF/DF the bispecific antibody B formed with high level of disulfide bond formation.

Both this study and the stydy described in Example 2 demonstrated that oxygen was not necessary during the UF/DF step for reformation of the disulfide bridges during Fab-arm exchange.

Conclusion: Maintaining levels of $DO_2$ at <4% during UF/DF step of manufacturing the bispecific antibody B using Fab-arm exhcange did not significantly affect disulfide bond formation. At completion of the UF/DF, Non-Reduced cSDS demonstrated % Purity>97%.

Example 5

Bispecific Antibody A Manufacturing in Low $DO_2$ in the Presence of EDTA During UF/DF During manufacturing of bispecific antibodies there are opportunities for free metal ions to be introduced to the manufacturing process. During the preparation of buffers via raw materials and the leaching from metallic components, these free metal ions may become involved in the redox reactions of the Fab-arm exchange. To investigate the possible effects of trace metals in the Fab-arm exchange, addition of EDTA during the Fab-arm exchange was studied. EDTA addition sequestered possible free metal ions in the solution which may catalyze the oxidative reaction for the reformation of disulfide bonds.

A solution was pepared using p1A-IgG4PAAF405R409 and p2A-IgG4PAAL405K409 at a molar ratio of 1.05:1.00. The mixture was then adjusted to pH 7.3 and diluted to a total IgG concentration of 10.5 g/L using 101 mM sodium acetate, 105 mM Tris Base, pH 7.3. A 50 mM Sodium Acetate, 800 mM 2-MEA pH 5.0 stock solution was added to the parental mAb mixture. The final reduction buffer composition piror to UF/DF was about 100 mM sodium acetate, about 35 mM 2-MEA, about 30 mM NaCl, pH 7.3.

The reduced parental solution was incubated for 23.5 hrs at 24° C. At the completion of the incubation, 500 mM EDTA, pH 8.0 stock solution was added to the reduced parental mixture to a target of 2 mM EDTA to chelate free metal ions that would be present in solution prior to the start of UF/DF. EDTA was also added to the diafiltration buffer to target of 100 mM Tris-Acetate, 30 mM NaCl, 2 mM EDTA, pH 7.5. This was done to ensure that additional free metal ions could not be introduced during the UF/DF buffer exchange. EDTA was not added during reduction step to allow any possible oxidation of disulfides and cystamine formation which may occur spontaneously during the step.

The reduced parental solution containing EDTA was subsequently transferred to the UF/DF retentate vessel and prior to the start of the UF, an overlay of nitrogen was delivered to the retentate vessel via the headspace of the vessel to deplete $DO_2$ from the retentate and was maintained throughout the entirety of the UF and DF process. To prevent the addition of $DO_2$ through the diafiltration buffer, the diafiltration buffer was sparged with nitrogen throughout processing. In-line $DO_2$ sensors verified that the retentate $DO_2$ levels reached levels below 2% $DO_2$ and the diafiltration buffer reached $DO_2$ levels below 1% $DO_2$ prior to the start of the UF and DF steps.

Throughout the UF and DF process, $DO_2$ levels were measured in the feed inlet, retentate, and permeate lines during the UF/DF and were all maintained <4% $DO_2$. The diafiltration buffer was maintained at levels <1% $DO_2$. The UF/DF system was maintained at a 58 mL/min crossflow rate, targeting a transmembrane pressure of 14.5 psi for 11 diafiltration volumes (DV). All processes following the incubation were performed at room temperature (18-22° C.). Upon completion of the UF/DF, a 9 mL sample was taken, remained unadjusted at pH 7.5, and immediately stored at −70° C. to prevent further oxidation. The remaining bulk of the recovered retentate was quenched with 1.0 M Acetic Acid and adjusted to pH 5.0, to minimize further disulfide bond formation. The bulk bispecific antibody sample at pH 5.0 was subsequently stored at −70° C. No buffer recovery flush was performed following the completion of UF/DF to prevent possible oxidation of the material from the introduction of the additional diafiltration buffer. Table 7 summarizes the UF/DF process parameters and performance.

TABLE 7

| Final 2-MEA Concentration (mM) | 35.0 |
| TMP (psi) | 14.8-15.5 |
| Crossflow (mL/min) | 58 |
| Diafiltration Concentration (g/L) | 25.0 |
| Total Diafiltration Volumes (DVs) | 11 |
| Mean Permeate Flux (L/m2/hr) | 30.9 |
| Load ratio (g/m2) | 318 |
| Yield (%) | N/A |

Non-Reduced cSDS analysis was used to measure the disulfide bond integrity in the formed bispecific antibody for both the frozen sample at pH 7.5 and the bulk material at pH 5.0. Purity of the pH 7.5 bispecific antibody preparation was 97.44% and purity of the bispecific antibody preparation at pH 5.0 was measured to be 97.39%.

This study demonstrated that under low % $DO_2$ environment during UF/DF and minimal available free metal ions the bispecific antibody A formed with high levels of disulfide bond formation. The study demonstrated that free metal ions for catalyzing the oxidative reaction may not be needed during UF/DF of Fab-arm exchange.

Conculsion: Experimental results demonstrated that the addition of EDTA to the reduced parental mixture prior to UF/DF in Fab-arm exchange did not affect disulfide bond formation. At completion of UF/DF, Non-Reduced cSDS resulted in % purity >97%.

Example 6

Comparison of Fab-Arm Exchange in Ambient and Low $DO_2$ Conditions During Reduction and UF/DF This study was designed to evaluate the hypothesis that some $DO_2$ mediated oxidation could be occurring during the 2-MEA Reduction.

Figure 8:
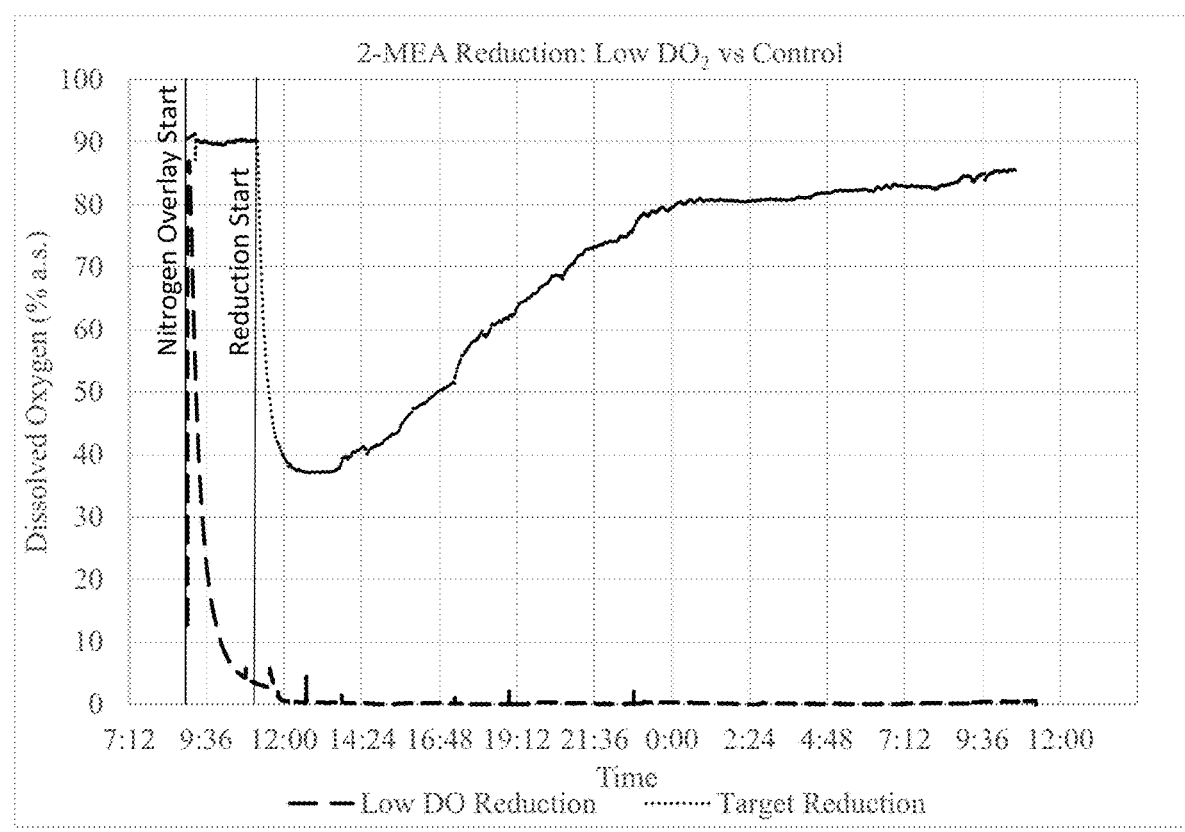
FIG. 8 shows percent (%) $DO_2$ over time during reduction in low $DO_2$ conditions (Low DO reduction) or at ambient $DO_2$ (target reduction). a.s.: air saturated.

For the study, Fab-arm exchange was conducted using parental antibodies p1B-IgG4PAAF405R409 and p2B-IgG4PAAL405K409. A mixture of p1B-IgG4PAAF405R409 and p2B-IgG4PAAL405K409 in solution was prepared and adjusted to pH 7.3 and diluted to a total IgG concentration of 10.5 g/L using 101 mM sodium acetate, 105 mM Tris Base, pH 7.3. The mixture containing the parental antibodies was divided into two separate vessels. In one vessel, an overlay of nitrogen was delivered to the vessel via the headspace to deplete $DO_2$ from the parental mixture until a % $DO_2$<5% was achieved. The other parental mixture vessel remained under ambient air conditions as a control for the reduction. A 50 mM Sodium Acetate, 800 mM 2-MEA pH 5.0 stock solution was added to each of the parental mixtures. The final reduction buffer composition piror to UF/DF was about 100 mM sodium acetate, about 35 mM 2-MEA, about 30 mM NaCl, pH 7.3. Both reduced parental solutions were incubated for 24 hrs at 24° C. and the % $DO_2$ was measured for both vessels, the results of which ar shown in FIG. 8. The low % $DO_2$ reduction vessel was maintained under an overlay of nitrogen throughout the entirety of the incubation and remained at <2% $DO_2$ for the 24 hrs. There was an initial drop in % $DO_2$ following 2-MEA spike to approximately 40% $DO_2$ in the vessel which remained under ambient air, after which % $DO_2$ gradually increased linearly back to >90% $DO_2$. The summary of UF/DF process paramteters and performance is shown in Table 8.

TABLE 8

| Final 2-MEA Concentration (mM) | 35.0 |
| TMP (psi) | 14.5-16.0 |
| Crossflow (mL/min) | 55 |
| Diafiltration Concentration (g/L) | 25.0 |
| Total Diafiltration Volumes (DVs) | 12 |
| Mean Permeate Flux (L/m2/hr) | 19.5 |
| Load ratio (g/m2) | 251 |
| Yield (%) | N/A |

During reduction, samples were obtained from both vessels though a sampling port on the vessel. The port was flushed prior to each sample draw and samples were immediately quenched by an addition of 10% v/v of cystamine RP-HPLC mobile phase, 20 mM Hexane Sulfonate, pH 2.0, buffer and each sample was verified to have been reduced to a pH<5 prior to analysis. All timepoints were assayed for disulfide bond integrity by Non-Reduced cSDS and residual 2-MEA/Cystamine concentration by RP-HPLC.

Additional sample preparation was required for residual 2-MEA/Cystamine analysis involving removal of the antibody by 5 kDa molecular weight retention filter. Non-Reduced cSDS % purity and residual 2-MEA/Cystamine results are reported in Table 9.

At the completion of the 24 hr reduction incubation, the low % $DO_2$ vessel was transferred to the UF/DF system. An overlay of nitrogen was continued to be delivered to the retentate vessel via the headspace of the vessel to continue depleting $DO_2$ from the retentate and was maintained throughout the entirety of the UF and DF process. The diafiltration buffer was also spared with nitrogen throughout processing, to prevent the addition of $DO_2$ through the buffer. In-line $DO_2$ sensors were used to verify that the retentate had reached levels below 5% $DO_2$ and the diafiltration buffer had reached levels below 1% $DO_2$ prior to the start of the UF and DF steps.

Throughout the UF and DF process, the $DO_2$ levels were measured in the feed inlet, retentate, and permeate lines during the UF/DF and were all maintained at <4% $DO_2$. The diafiltration buffer was maintained at levels <1% $DO_2$. The UF/DF system was maintained at a 55 mL/min crossflow rate, targeting a transmembrane pressure of 14.5 psi for 12 diafiltration volumes (DV) using a 100 mM Tris-Acetate, 30 mM NaCl, pH 7.5 buffer. All processes following the incubation were performed at room temperature (18-22° C.). Upon completion of UF/DF, the recovered retentate was quenched with 1.0 M acetic acid and adjusted to pH 5.0, to minimize further disulfide bond formation. The bulk material was subsequently stored at −70° C. No additional buffer recovery flush was performed following the completion of UF/DF to prevent any possible oxidation of the material from the introduction of the additional diafiltration buf.

Disulfide integrity by Non-Reduced cSDS and residual 2-MEA/Cysteamine by RP-HPLC was measured at various timepoints throughout reduction and UF/DF for both the low $DO_2$% vessel and the control vessel with ambient $DO_2$.

Summary of data is shown in Table 9. Only the Fab-arm exchange reactions under oxygen deprived conditions was continued through UF/DF in this experiment. Residual 2-MEA and cystamine was measured only through the reduction for both Fab-arm exchange conditions, however during the UF/DF for the oxygen deprived conditions, samples were obtained to measure the possible reformation of disulfide bonds by Non-Reduced cSDS.

Conclusion: This data supports the hypothesis that oxygen independent pathways mediate disulfide bond formation in the absence of oxygen during the reduction and UF/DF.

When Fab-arm exchange was performed under oxygen-deprived conditions, minimal cystamine formation and disulfide bond reformation was observed over the course of the reduction. By the completion of the 24 hr incubation in the presence of 2-MEA, only 1.6 mM Cystamine and 14.74% intact antibody was observed. Nevertheless, once the antibody sample was processed through UF/DF, increasing levels of disulfide bond reformation was evident as 2-MEA was removed. At the end of DV (at DV12), the formed bispecific antibody preparation at pH 5.0 was measured to be % Purity of 90.59%.

In ambient $DO_2$, disulfide bond reduction occurred quickly, 30 min after start of the reduction about 86% of the parental antibodies were reduced. Reformation of the disulfide bonds was observed during the remainder of the reduction, even in the continued presence of residual 2-MEA in solution. At the completion of reduction phase, 71% of the antibodies had intact disulfide bonds. Cystamine dimer formation as well as increasing levels of formation of the bispecific antibody during the reduction incubation indicated that oxygen was being consumed by Reactions 4 and 2, respectively, illustrated in FIG. 4. This was supported by the RP-HPLC data which showed significant depletion of 2-MEA and conversion to the dimer compound cystamine (Reaction 4 in FIG. 4).

This study demonstrated that $DO_2$ during the reduction stage catalyzed the formation of IgG HC-HC and LC-HC interchain disulfide bonds, but was not essential for the formation of an intact bispecific antibody as the disulfide bonds were reformed even under oxygen-deprived conditions. Removal of 2-MEA, even under the absence of oxygen, during diafiltration accounted for the disulfide bond reformatio, driven by the reverse reaction in Reaction 1 in FIG. 4.

TABLE 9

|  | Low $DO_2$ | | | | Ambient $DO_2$ | | | |
| --- | --- | --- | --- | --- | --- | --- | --- | --- |
| Timepoint | cSDS (%) | 2-MEA (mM) | Cystamine (mM) | $DO_2$ (%) | cSDS (%) | 2-MEA (mM) | Cystamine (mM) | $DO_2$ % |
| t = 0* | 98.34 | N/a | N/a | 2.5 | 98.08 | N/a | N/a | 90 |
| t = 3 min | 23.5 | 33.3 | 0.5 | 4 | 44.85 | 35.3 | 0.4 | 85 |
| t = 10 min | 10.9 | 31.8 | 0.5 | 1.4 | 24.19 | 35.5 | 0.6 | 77 |
| t = 30 min | 4.57 | 31.1 | 0.5 | 1 | 14.22 | 34.8 | N/a | 63 |
| t = 1 hr | 2.86 | 30.6 | 0.5 | <1 | 19.13 | 33.7 | 1.4 | 38 |
| t = 2 hr | 2.74 | 31.8 | 0.6 | <1 | 41.16 | 31.1 | 2.7 | 37 |
| t = 4 hr | 3.37 | 31.9 | 0.8 | <1 | 53.07 | 27.6 | 4.0 | 50 |
| t = 6 hr | 4.17 | 32.2 | 0.8 | <1 | 56.02 | 25.1 | 5.1 | 63 |
| t = 8 hr | 4.92 | 32.2 | 0.8 | <1 | 59.66 | 23.3 | 6.0 | 70 |
| t = 10 hr | 5.85 | 33.1 | 0.9 | <1 | 61.32 | 21.9 | 6.9 | 75 |
| t = 12 hr | 6.96 | 32.2 | 0.9 | <1 | 65.15 | 20.0 | 7.5 | 80 |
| t = 22 hr | 14.64 | 32.4 | 1.2 | <1 | 62.82 | 15.4 | 10.5 | 85 |
| t = 24 hr | 14.74 | 32.1 | 1.6 | <1 | 71.00 | 14.3 | 10.4 | 92 |
| DV0 | 27.60 | | | | | | | |
| DV2 | 75.69 | | | | | | | |
| DV4 | 85.64 | | | | | | | |
| DV6 | 82.54 | | | | | | | |
| DV8 | 90.38 | | | | | | | |
| DV12 | 89.90 | | | | | | | |
| FINAL | 90.59 | | | | | | | |

*Initial t = 0 sample was taken immediately following the 2-MEA spike of the parental mixture. Sample time points were taken to determine the rate of reduction and reformation of disulfide bonds during both the reduction and UF/DF

Example 7

Generation of Bispecific EGFR/c-Met Antibody Using Fab-Arm Exchange in Ambient DO$_2$ Utilizing High Concentrations of Parental Antibodies This study was designed to evaluate the hypothesis that higher homodimeric mixture protein concentrations and varying ratio of reducing agent to protein mass produces oxidized heterodimer antibody.

A bispecific EGFR/cMet antibody was used in the study. The EGFR/cMet antibody comprises a first heavy chain (HC1) of SEQ ID NO: 4, a first light chain (LC) of SEQ ID NO: 5, a second HC (HC2) of SEQ ID NO: 6 and a second LC (LC2) of SEQ ID NO: 7.

For the study, Fab-arm exchange was conducted using parental EGFR and c-Met antibodies (both were IgG1 isotypes). A mixture of the parental antibodies filtered neutralized protein A eluates in solution was prepared and adjusted to pH 7.9 and diluted to a total IgG concentration of 10-35 g/L using 209.5 mM sodium acetate, 300 mM NaCl, pH 7.9. A 50 mM Sodium Acetate, 800 mM 2-MEA pH 5.0 stock solution was added to each of the parental mixtures to a target reductant concentration of 35, 50, or 100 mM. Both reduced parental solutions were incubated for 3 hrs controlled at either 21.5° C., 24° C., or left uncontrolled at ambient room temperature. After 3 hours the incubated mixtures were ultrafiltered and diafiltered against 10 mM Tris, 7.8 mM Acetic acid, pH 7.5. The summary of operating conditions and analytical results are shown in Table 10. This study demonstrated oxidized heterodimer under these conditions for a temperature range of 21.5-24° C., reductant concentrations of 35-100 mM, and homodimeric mixture protein concentration of 10-35 g/L. Bispecific antibody integrity and purity was assessed by both NR-cSDS and IHC-HPLC using methods described in Example 1.

TABLE 10

| Run number | Reduction Incubation Time (hours) | Reduction Incubation Temp | [2MEA] (mM) | [Protein] g/L | NR-cSDS (%) | HIC-HPLC (%) |
|---|---|---|---|---|---|---|
| 1 | 24 | 24 | 35 | 10.5 | 96.01 | |
| 2 | 24 | 24 | 35 | 10.5 | 94.63 | |
| 3 | 3 | 24 | 50 | 10.5 | 96.74 | 92.2 |
| 4 | 3 | 24 | 50 | 10.5 | 96.95 | 90.1 |
| 5 | 3 | 24 | 100 | 10.5 | 95.85 | 93.2 |
| 6 | 3 | 21.5 | 100 | 30 | 96.46 | 92.2 |
| 7 | 3 | 21.5 | 100 | 35 | 96.33 | 92.1 |
| 8 | 3 | 24 | 100 | 30 | 96.77 | |
| 9 | 3 | RT | 100 | 35 | 95.96 | |
| 10 | 3 | RT | 100 | 35 | 96.86 | |
| 11 | 8 | RT | 100 | 35 | 96.66 | |
| 12 | 3 | RT | 100 | 35 | 97.18 | 93.2 |
| 13 | 3 | RT | 100 | 35 | 97.01 | 93.2 |

(HC1)

SEQ ID NO: 4

QVQLVESGGGVVQPGRSLRLSCAASGFTFSTYGMHWVRQAPGKGLEWV
AVIWDDGSYKYYGDSVKGRFTISRDNSKNTLYLQMNSLRAEDTAVYYC
ARDGITMVRGVMKDYFDYWGQGTLVTVSSASTKGPSVFPLAPSSKSTS
GGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSD
IAVEWESNGQPENNYKTTPPVLDSDGSFLLYSKLTVDKSRWQQGNVFS
CSVMHEALHNHYTQKSLSLSPGK (LC1)

SEQ ID NO: 5

AIQLTQSPSSLSASVGDRVTITCRASQDISSALVWYQQKPGKAPKWYD
ASSLESGVPSRFSGSESGTDFTLTISSLQPEDFATYYCQQFNSYPLTF
GGGTKVEIKRTVAAPSVFIFPPSDEQLKSGTASVVCLLNNFYPREAKV
QWKVDNALQSGNSQESVTEQDSKDSTYSLSSTLTLSKADYEKHKVYAC
EVTHQGLSSPVTKSFNRGEC (HC2)

SEQ ID NO: 6

QVQLVQSGAEVKKPGASVKVSCETSGYTFTSYGISWVRQAPGHGLEWM
GWISAYNGYTNYAQKLQGRVTMTTDTSTSTAYMELRSLRSDDTAVYYC
ARDLRGTNYFDYWGQGTLVTVSSASTKGPSVFPLAPSSKSTSGGTAAL
GCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWE
SNGQPENNYKTTPPVLDSDGSFFLYSRLTVDKSRWQQGNVFSCSVMHE
ALHNHYTQKSLSLSPGK (LC2)

SEQ ID NO: 7

DIQMTQSPSSVSASVGDRVTITCRASQGISNWLAWFQHKPGKAPKLLI
YAASSLLSGVPSRFSGSGSGTDFTLTISSLQPEDFATYYCQQANSFPI
TFGQGTRLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

We claim:

1. A method of producing a heterodimeric antibody, comprising
   a) providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that the heterodimeric interaction between the first CH3 region and the second CH3 region is stronger than a homodimeric interaction between the first CH3 region or a homodimeric interaction between the second CH3 region;
   b) combining the first homodimeric antibody and the second homodimeric antibody into a mixture;
   c) incubating the mixture in the presence of a reducing agent;
   d) removing the reducing agent to produce the heterodimeric antibody, and
   e) controlling percentage saturation of dissolved oxygen (% $DO_2$) to be 15% or less in step d), wherein 15% $DO_2$ is equivalent to 1.44 mg/L or 45 µM $DO_2$.

2. The method of claim 1, wherein the % $DO_2$ in the mixture in step d) is about 10% or less, about 9% or less, about 8% or less, about 7% or less, about 6% or less, about 5% or less, about 4% or less, about 3% or less, about 2% or less or about 1% or less.

3. The method of claim 2, wherein % $DO_2$ is controlled by an overlay of nitrogen.

4. The method of claim 3, wherein the first homodimeric antibody and the second homodimeric antibody are combined into the mixture in step b) at a molar ratio of between about 1:1 to about 1:2.

5. The method of claim 3, wherein the first homodimeric antibody and the second homodimeric antibody are combined into the mixture in step b) at the molar ratio of about 1.05:1.

6. The method of claim 1, wherein total concentration of immunoglobulin in the mixture is about 10.5 g/L.

7. The method of claim 6, wherein the mixture is incubated in the presence of the reducing agent for about 10 minutes or longer.

8. The method of claim 7, wherein the mixture is incubated in the presence of the reducing agent from about 10 minutes to about 24 hours.

9. The method of claim 7, wherein the reducing agent is 2-mercaptoethylamine (2-MEA), a chemical derivative of 2-MEA, L-cysteine or D-cysteine.

10. The method of claim 9, wherein concentration of 2-MEA in the mixture is about 35 mM.

11. The method of claim 9, wherein the mixture comprises a buffer.

12. The method of claim 11, wherein the buffer comprises a sodium acetate buffer.

13. The method of claim 12, wherein the buffer further comprises NaCl.

14. The method of claim 13, wherein the buffer comprises about 100 mM sodium acetate and about 30 mM NaCl.

15. The method of claim 14, wherein the pH of the buffer is about 7.3.

16. The method of claim 1, wherein the reducing agent is removed by filtration.

17. The method of claim 16, wherein the filtration is diafiltration.

18. The method of claim 1, wherein the first homodimeric antibody and the second homodimeric antibody are an IgG1, IgG2 or IgG4 isotype.

19. The method of claim 18, wherein the first CH3 domain and the second CH3 domain comprise following mutations when compared to the wild-type IgG1 of SEQ ID NO: 1, wild-type IgG2 of SEQ ID NO: 2 or wild-type IgG4 of SEQ ID NO: 3: F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/

K409AGRH, Y407LWQ/K409AGRH, T366Y/F405A, T366W/F405W, F405W/Y407A, T394W/Y407T, T394S/Y407A, T366W/T394S, F405W/T394S, T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, T350V_L351Y_F405A_Y407V/T350V_T366L_K392L_T394W, K409D/D399K, K409E/D399R, K409D_K360D/D399K_E356K, K409D_K360D/D399E_E356K, K409D_K370D/D399K_E357K, K409D_K370D/D399E_E357K, K409D_K392D/D399K_E356K_E357K or K409D_K392D/D399E_E356K_E357K, wherein the amino acid positions are numbered according to the EU Index.

20. The method of claim 19, wherein the first Fc region and/or the second Fc region comprise one or more mutations when compared to the wild-type IgG1 of SEQ ID NO: 1, wild-type IgG2 of SEQ ID NO: 2 or wild-type IgG4 of SEQ ID NO: 3 that modulate binding of the first Fc region and/or the second Fc region to an Fcγ receptor (FcγR), an FcRn, or to protein A.

21. The method of claim 20, wherein the FcγR is FcγRI, FcγRIIa, FcγRIIb or FcγRIII.

22. The method of claim 20, wherein the one or more mutations that modulate binding of the first Fc region and/or the second Fc region to the Fcγ receptor are L234A_L235A, F234A_L235A, S228P_F234A_L235A, S228P_L234A_L235A, V234A_G237A_P238S_H268A_V309L_A330S_P331S, V234A_G237A, H268Q_V309L_A330S_P331S, S267E_L328F, L234F_L235E_D265A, L234A_L235A_G237A_P238S_H268A_A330S_P331S or S228P_F234A_L235A_G237A_P238S, wherein the amino acid positions are numbered according to the EU Index.

23. The method of claim 20, wherein the one or more mutations that modulate binding of the first Fc region and/or the second Fc region to the FcRn are M428L_N434S, M252Y_S254T_T256E, T250Q_M428L, N434A_T307A_E380A_N434A, H435A, P257I_N434H, D376V_N434H, M252Y_S254T_T256E_H433K_N434F, T308P_N434A or H435R, wherein the amino acid positions are numbered according to the EU Index.

24. The method of claim 20, wherein the one or more mutations that modulate binding of the first Fc region and/or the second Fc region to protein A are Q311R, Q311K, T307P_L309Q, T307P_V309Q, T307P_L309Q_Q311R, T307P_V309Q_Q311R, H435R or H435R_Y436F, wherein the amino acid positions are numbered according to the EU Index.

25. The method of claim 1, wherein the steps of producing the heterodimeric antibody are conducted under GMP-compliant conditions.

26. The method of claim 25, wherein the steps of producing the heterodimeric antibody are conducted during manufacture of a drug substance comprising the heterodimeric antibody.

27. The method of claim 1, wherein the heterodimeric antibody is a bispecific antibody.

28. The method of claim 27, wherein the bispecific antibody binds CD3, CD123, BCMA, EGFR or c-Met, or any combination thereof.

29. The method of claim 1, wherein a mass ratio of the reducing agent to total immunoglobulin in the mixture is between about 1.0 and about 5.0.

30. The method of claim 29, wherein the mass ratio is between about 1.4 and about 3.8.

31. The method of claim 29, wherein the mass ratio is between about 3.3 and about 4.4.

32. The method of claim 1, wherein the % $DO_2$ in the mixture is about 10% or less in step d).

33. The method of claim 1, wherein the % $DO_2$ in the mixture is about 5% or less in step d).

34. A method of producing a heterodimeric antibody, comprising
  a) providing a first homodimeric antibody comprising a first Fc region of an immunoglobulin comprising a first CH3 region and a second homodimeric antibody comprising a second Fc region of an immunoglobulin comprising a second CH3 region, wherein the amino acid sequences of the first CH3 region and the second CH3 regions are different and are such that the heterodimeric interaction between the first CH3 region and the second CH3 region is stronger than a homodimeric interaction between the first CH3 region or a homodimeric interaction between the second CH3 region;
  b) combining the first homodimeric antibody and the second homodimeric antibody into a mixture;
  c) incubating the mixture in the presence of a reducing agent;
  d) removing the reducing agent to produce the heterodimeric antibody, and
  e) controlling the concentration of oxygen to be 0.480 mg/L or less, or 14.99 μM or less, in step d).

35. The method of claim 1, wherein the % $DO_2$ in the mixture in step d) is about 4% or less.

36. The method of claim 1, wherein the % $DO_2$ in the mixture in step d) is about 3% or less.

* * * * *

SEQUENCE LISTING

<160> NUMBER OF SEQ ID NOS: 7

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 455
<212> TYPE: PRT
<213> ORGANISM: Artificial Sequence
<220> FEATURE:
<223> OTHER INFORMATION: HC1 of EGFR/cMet antibody

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 5
<211> LENGTH: 214
<212> TYPE: PRT
<213> ORGANISM: Artificial Sequence
<220> FEATURE:
<223> OTHER INFORMATION: LC1 of EGFR/cMet antibody

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 449
<212> TYPE: PRT
<213> ORGANISM: Artificial Sequence
<220> FEATURE:
<223> OTHER INFORMATION: HC2 of EGFR/cMet antibody

<400> SEQUENCE: 6

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 7
<211> LENGTH: 214
<212> TYPE: PRT
<213> ORGANISM: Artificial Sequence
<220> FEATURE:
<223> OTHER INFORMATION: LC2 of EGFR/cMet antibody

<400> SEQUENCE: 7

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Ala Asn Ser Phe Pro Ile
             85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```